(12) United States Patent
Westaway et al.

(10) Patent No.: US 6,893,866 B1
(45) Date of Patent: May 17, 2005

(54) FLAVIVIRUS EXPRESSION AND DELIVERY SYSTEM

(75) Inventors: Edwin G. Westaway, Herston (AU); Alexander A. Khromykh, Herston (AU); Andrei Varnavski, Herston (AU)

(73) Assignee: The Crown in the Right of the Queensland Department of Health, Herston (AU)

( * ) Notice: Subject to any disclaimer, the term of this patent is extended or adjusted under 35 U.S.C. 154(b) by 0 days.

(21) Appl. No.: 09/580,476

(22) Filed: May 26, 2000

Related U.S. Application Data

(63) Continuation of application No. PCT/AU98/00993, filed on Nov. 30, 1998.

(30) Foreign Application Priority Data

Nov. 28, 1997 (AU) ............................................... PP0627
Sep. 23, 1998 (AU) ............................................... PP6096

(51) Int. Cl.$^7$ ........................ C12N 15/86; C12N 15/63; C12N 15/64; C12N 15/40
(52) U.S. Cl. ............................... 435/320.1; 435/235.1; 435/69.1; 536/23.1; 536/23.72; 536/24.1
(58) Field of Search ............................... 435/69.1, 325, 435/366, 320.1, 235.1, 5, 6, 91.32, 91.33, 91.4, 91.41, 91.42, 352, 455, 456, 457; 424/93.1, 93.2, 93.6; 536/23.1, 23.72, 24.1

(56) References Cited

PUBLICATIONS

Yamshchikovv, et al., Virology, 281, 294 (2001).
Barba et al., "Bicistronic Flavivirus replicons based on tallow fever 17D," p. 33 of the abstract book from the 6$^{th}$ International Symposium on Hepatitis C and Related Viruses, NIII, Bethesda, Maryland, Jun. 6–9 (1999).
Barba et al., "Engineering yellow fever 17D for heterologous gene expression and vaccination," P6–5, p. 149 of the abstract book of the 19$^{th}$ annual meeting of American Society for Virology, Fort Collins, Colorado, Jul. 8–12 (2000).
Khromykh et al., "Essential Role of Cyclization Sequences in Flavirus RNA Replication", Journal of Virology, Jul. 2001, p. 6719–6728.
Shoji et al., (1997) *J. Gen. Virol.*, 78:2657–2664.
Khromykh and Westaway, *J. Virol.*, 1994, 63:4580–4588.
Khromykh and Westaway, *J. Virol.*, 1997, 71:1497–1505.
Trowbridge and Gowans, *Arch. Virol.*, 1998, 143:501–511.
Rees et al., *Bio Techniques*, 1996, 20:102–110.
Percy et al., *J. Virol.*, 1994, 68:4486–4492.
Westaway, et al., *J. Virol.*, 1997, 71:6650–6661.
Baker et al., *J. Biol. Chem*, 269:25381–25386.
Perrotta and Been, 191 *Nature* (London) 350:434–436.
Karreman, 1998, *BioTechniques* 24:736–742.
Khromykh et al., *J. Virol.*, 1998, 72:5967–5977.
Galler et al., *Brazilian J. Med and Biol Res.*, 1997, 30:157–168.
Lindenbach et al., *J. Virol.*, 1997, 12:9608–9617.

*Primary Examiner*—David Guzo
(74) *Attorney, Agent, or Firm*—Fredrikson & Byron, P.A.

(57) ABSTRACT

The present invention provides a gene expression system comprising: a) a self-replicating expression vector of flavivirus origin which includes the flavivirus 5' untranslated region (UTR), at least a portion of the 5' coding region for flavivirus core protein, the nucleotide sequence coding for the flavivirus non-structural proteins, and the complete or most of the 3'-terminal sequence of the flavivirus 3'UTR, required for self-replication of flavivirus genomic material, which vector is adapted to receive at least a nucleotide sequence without disrupting its replication capabilities; and b) at least a second vector that is capable of expressing flavivirus structural protein(s) and any other proteins required for packaging of the self-replicating expression vector into flavivirus viral particles which vector is engineered to prevent recombination with the self-replicating vector when in its presence.

37 Claims, 20 Drawing Sheets

 
A
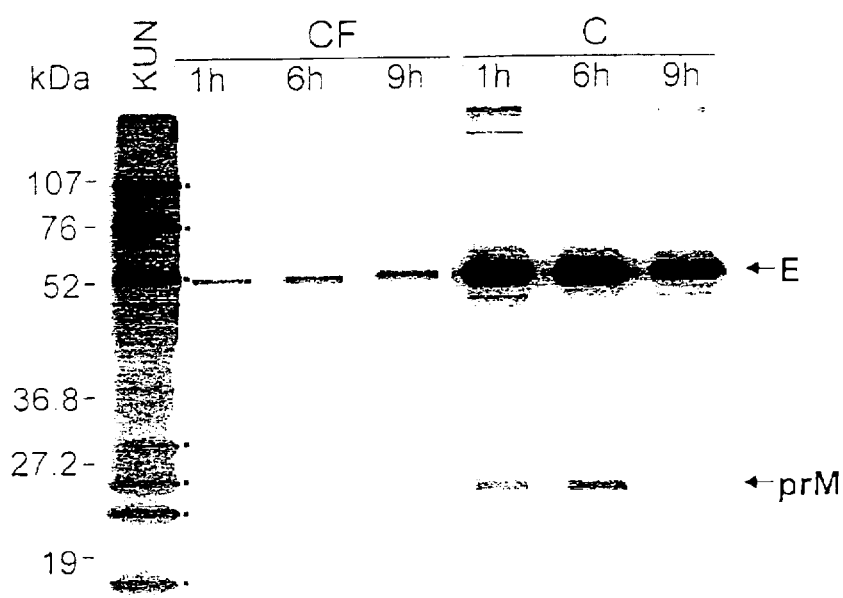
B
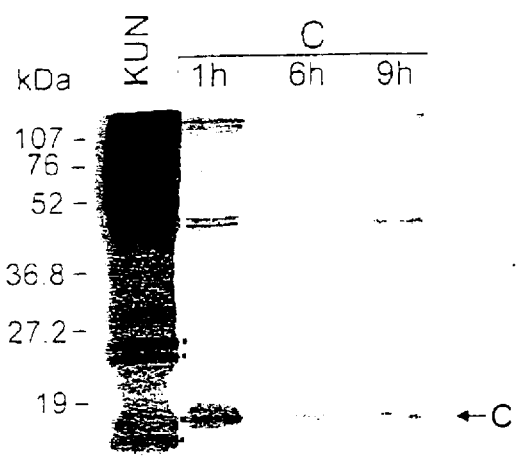
C
Fig. 5.

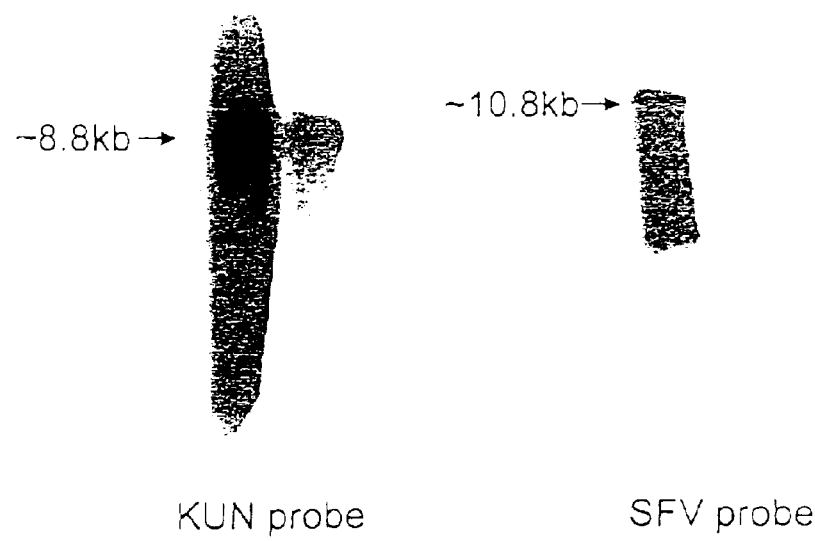
Fig. 6

9A
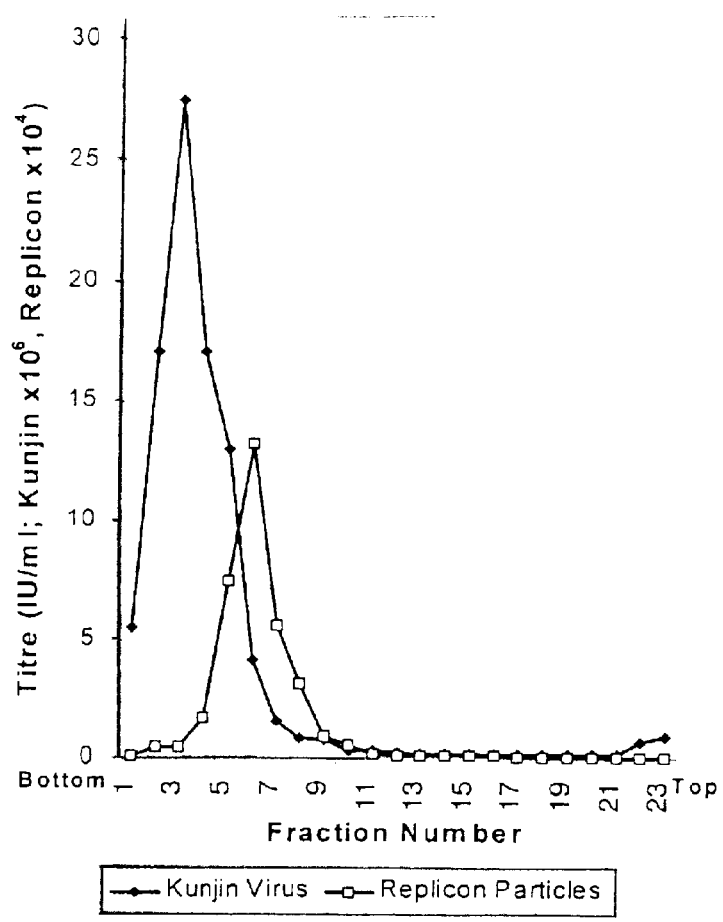
9B
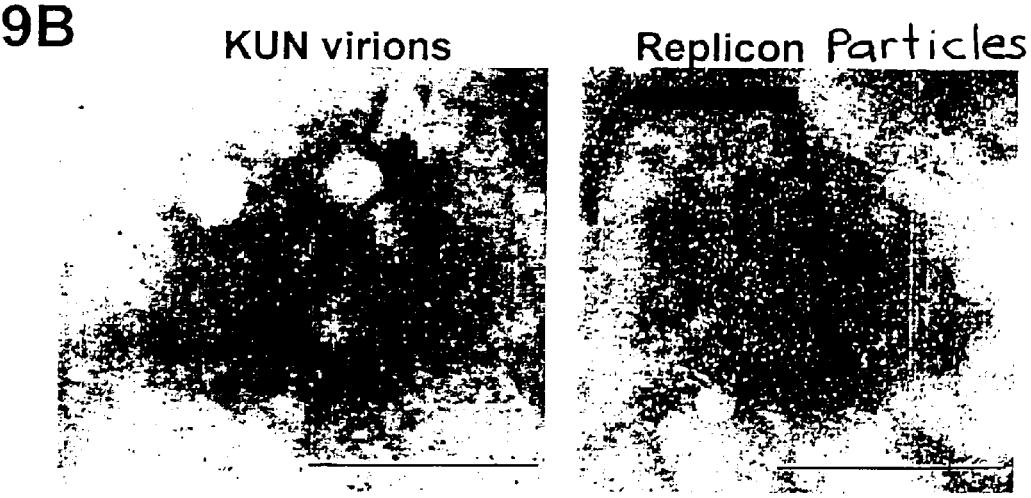
Fig. 9

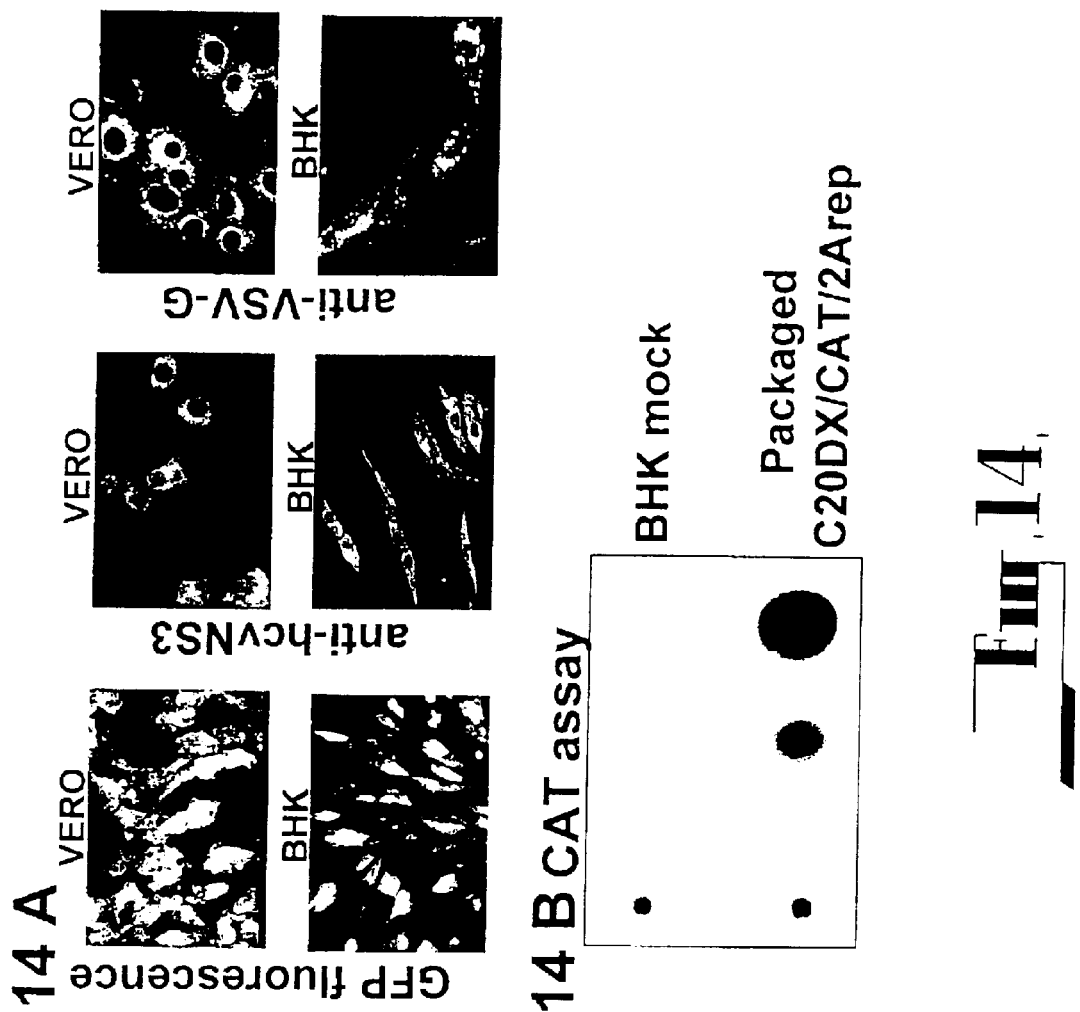

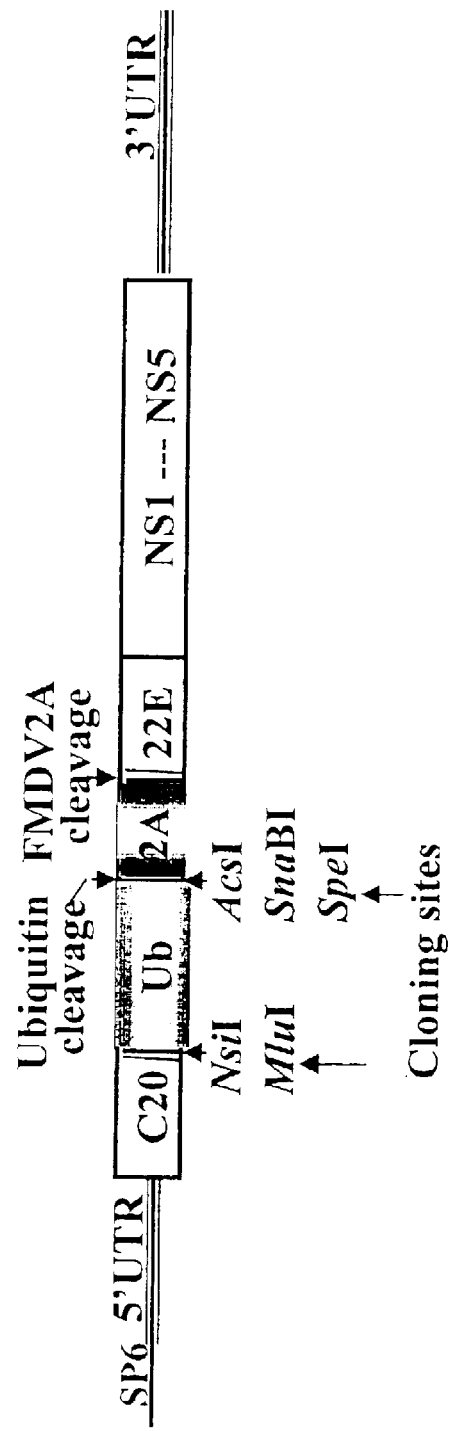
Fig. 16.

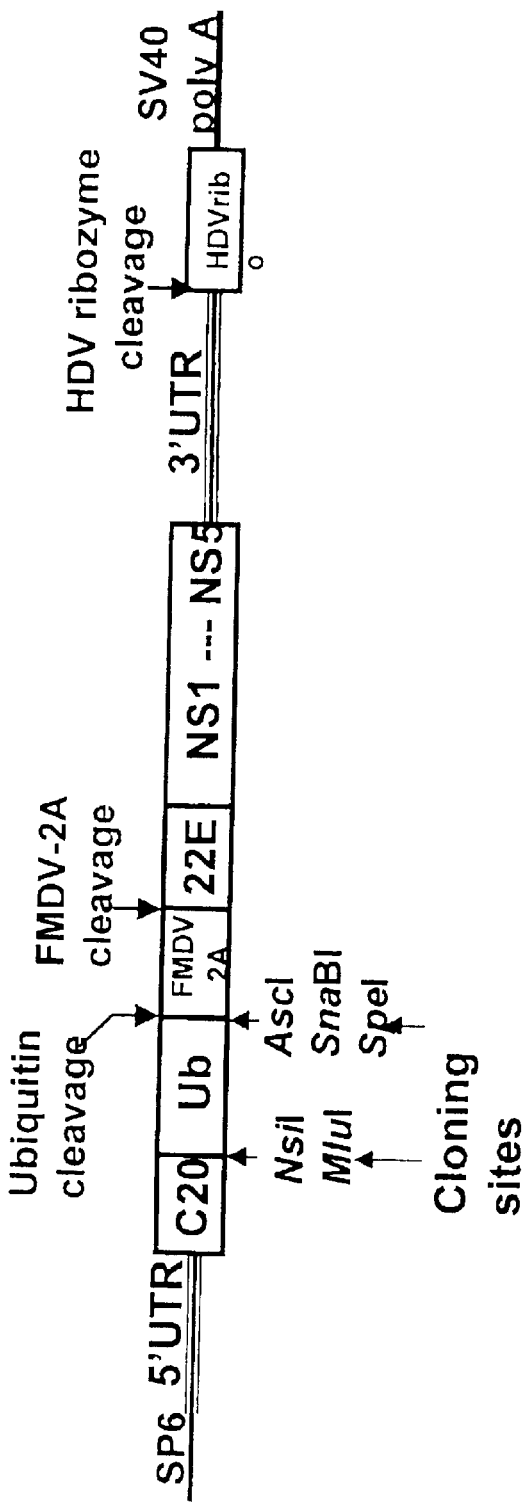
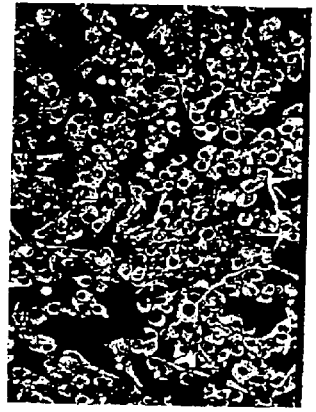
Fig. 17.

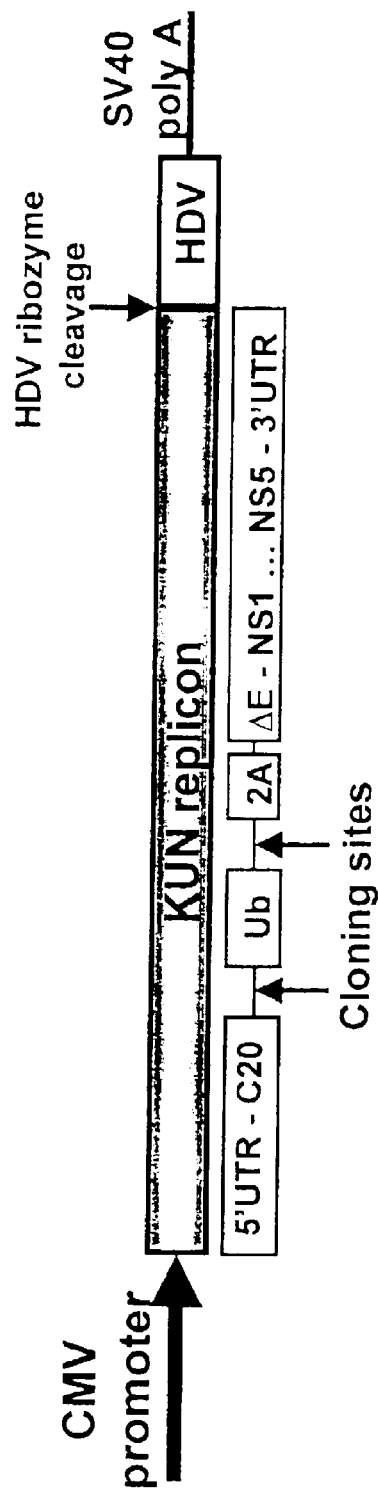
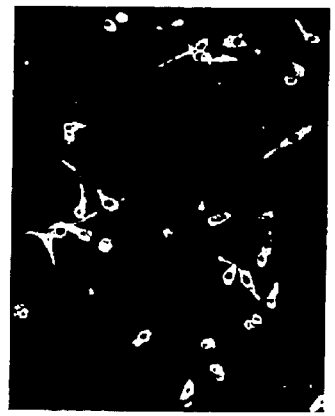
Fig. 18

```
                              SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
          (A) LENGTH: 26
          (B) TYPE: nucleic acid
          (C) STRANDEDNESS: single
          (D) TOPOLOGY: linear (xi) SEQUENCE DESCRIPTION: SEQ ID NO: 1:

CTGGTTAACT GTGTGGTAAA GCCCTT                                          26

(2) INFORMATION FOR SEQ ID NO: 2:

(i) SEQUENCE CHARACTERISTICS:
          (A) LENGTH: 32
          (B) TYPE: nucleic acid
          (C) STRANDEDNESS: single
          (D) TOPOLOGY: linear (xi) SEQUENCE DESCRIPTION: SEQ ID NO: 2:

GAGAACACAG GATCTGGGTC GGCATGGCAT CT                                   32

(2) INFORMATION FOR SEQ ID NO: 3:

(i) SEQUENCE CHARACTERISTICS:
          (A) LENGTH: 28
          (B) TYPE: nucleic acid
          (C) STRANDEDNESS: single
          (D) TOPOLOGY: linear (xi) SEQUENCE DESCRIPTION: SEQ ID NO: 3:

GGCCTCGAGC AATTGTTGTT GTTAACTT                                        28

(2) INFORMATION FOR SEQ ID NO: 4:

(i) SEQUENCE CHARACTERISTICS:
          (A) LENGTH: 30
          (B) TYPE: nucleic acid
          (C) STRANDEDNESS: single
          (D) TOPOLOGY: linear (xi) SEQUENCE DESCRIPTION: SEQ ID NO: 4:

GCGCTTAAGA CATTGATTAT TGACTAGTTA                                      30

(2) INFORMATION FOR SEQ ID NO: 5

(i) SEQUENCE CHARACTERISTICS:
          (A) LENGTH: 32
          (B) TYPE: nucleic acid
```

-continued (C) STRANDEDNESS: single
        (D) TOPOLOGY: linear (xi) SEQUENCE DESCRIPTION: SEQ ID NO: 5:

CGTTTAGTGA ACCGAGTAGT TCGCCTGTGT GA                32

(2) INFORMATION FOR SEQ ID NO: 6:

(i) SEQUENCE CHARACTERISTICS:
        (A) LENGTH: 29
        (B) TYPE: nucleic acid
        (C) STRANDEDNESS: single
        (D) TOPOLOGY: linear (xi) SEQUENCE DESCRIPTION: SEQ ID NO: 6:

GTGACGCGTC GGCCGGGCCC TGGGTTGGA                    29

(2) INFORMATION FOR SEQ ID NO: 7:

(i) SEQUENCE CHARACTERISTICS:
        (A) LENGTH: 14
        (B) TYPE: nucleic acid
        (C) STRANDEDNESS: single
        (D) TOPOLOGY: linear (xi) SEQUENCE DESCRIPTION: SEQ ID NO: 7:

GGATCTCGAT GTCT                                    14

(2) INFORMATION FOR SEQ ID NO: 8:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 8:

GGAGGGATCC CGGGTAATTA A                            21

(2) INFORMATION FOR SEQ ID NO: 9:

(i) SEQUENCE CHARACTERISTICS:
        (A) LENGTH: 27
        (B) TYPE: nucleic acid
        (C) STRANDEDNESS: single
        (D) TOPOLOGY: linear (xi) SEQUENCE DESCRIPTION: SEQ ID NO: 9:

GGATCTACCA TGGCACGCCT GGGAGGA                      27

(2) INFORMATION FOR SEQ ID NO: 10:

(i) SEQUENCE CHARACTERISTICS:
        (A) LENGTH: 13
        (B) TYPE: nucleic acid
        (C) STRANDEDNESS: single
        (D) TOPOLOGY: linear (xi) SEQUENCE DESCRIPTION: SEQ ID NO: 10:

CATGCTTAGA TCC                                     13

FLAVIVIRUS EXPRESSION AND DELIVERY SYSTEM

CROSS-REFERENCE TO RELATED APPLICATIONS

The present application is a continuation of International Application No. PCT/AU98/00993 (published as International Publication No. WO 99/28487), filed 30 Nov. 1998 and designating the United States, which in turn claims priority from Australian Application Nos. PP 0627, filed 28 Nov. 1997 and PP 6096, filed 23 Sep. 1998, the teachings of all of which are incorporated herein by reference.

The present invention generally relates to the field of gene expression and in particular to Flavivirus gene expression and delivery systems and to virus like particles produced from such systems.

Improved methodologies for maximising recombinant gene expression are an on-going effort in the art. Of particular interest is the development of methodologies that maximise recombinant expression of mammalian genes in safe vectors suitable for producing commercially useful quantities of biologically active proteins.

Currently, there are numerous expression systems available for the expression of genes. While procaryotic and yeast expression systems are extremely efficient and easy to use, these systems suffer from a number of disadvantages, including an inability to glycosylate proteins, inefficient cleavage of "pre" or "prepro" sequences from proteins (eg., inefficient post translational modification), and a general inability to secrete proteins.

Another expression system widely available is the baculovirus expression system. This system is arguably one of the most efficient in protein production, but is limited only to use in insect cell lines. Unfortunately, insect cell lines glycosylate proteins differently from mammalian cell lines thus this system has not proven useful for the production of many mammalian proteins. Another disadvantage of this system is that it relies on the use of homologous recombination for the construction of recombinant virus stocks. Thus, this system often proves very laborious when large numbers of genetic variants have to be analysed.

In view of these problems the art has sought eucaryotic host systems, typically mammalian host cell systems, for mammalian protein production. One feature of such systems is that the protein produced has a structure most like that of the natural protein species and purification often is easier since the protein can be secreted into the culture medium in a biologically active form. One of the most efficient mammalian cell expression systems is based on Vaccinia virus. The main problem with this system, however, is that it uses recombinant viruses that express the heterologous gene upon infection. Thus there is no control over the virus once it has been release.

Recently researchers have started to explore the use of positive strand RNA viruses such as Semliki Forest Virus (SFV), Sindbis (SIN) virus, and poliovirus, as vectors for expression of heterologous genes in vitro and in vivo. The success of these expression systems has been mainly based on each virus' ability to produce high titer stocks of "pseudo" infectious particles containing recombinant replicon RNA packaged by structural proteins. In commercially available Semliki Forest virus (SFV) and Sindbis virus expression systems this is achieved by co-transfection of replicon RNA with defective helper RNA(s) expressing structural genes, but lacking the packaging signal. Replicon RNA expression provides enzymes for RNA replication and transcription of both RNA's, whereas helper RNA supports the production of structural proteins for packaging of replicon RNA via expression of its subgenomic region. The main problem with these expression systems is that the viruses used in the expression system are cytopathic and often compete out the host protein synthesis. Another major disadvantage of these systems includes possible contamination with infectious particles containing packaged full-length genomic RNA (in other words, infectious virus) due to the high probability of recombination between replicon and helper RNAs.

The present invention seeks to provide an improved expression and delivery system that at least ameliorates some of the problems associated with prior art systems.

Throughout this specification, unless the context requires otherwise, the word "comprise", or variations such as "comprises" or "comprising" will be understood to imply the inclusion of a stated integer or group of integers, but not the exclusion of any other integer or group of integers including method steps.

SUMMARY OF THE INVENTION

The present invention provides a gene expression system comprising:

a) a replicon of flavivirus origin, which is adapted to receive at least a nucleotide sequence without disrupting its replication capabilities and which is unable to express at least part or all of a structural protein and or another protein(s) required for packaging of a flavivirus genome into a virus particle; and b) at least a second vector that is capable of expressing flavivirus structural protein(s) and/or any other proteins required for packaging of the self-replicating expression vector into flavivirus viral particles which vector is engineered to prevent recombination with the self-replicating vector when in its presence.

Any replicon (self-replicating expression vector) derived from any flavivirus RNA may be used in the present invention. The replicon should however encode a sufficient amount of a flavivirus 5' UTR and at least a portion of the 5' flavivirus coding region for core protein, each of which is required for RNA replication. Both the 5' UTR and the 5' core protein coding region of a flavivirus genome contains regulatory elements that are required for flavivirus RNA replication. It will be appreciated that the flavivirus 5' UTR and the 5' core protein coding region may contain mutations or deletions in these regions and still be able to replicate. Preferably, the replicon should contain 5' UTR and at least about between 60 and 80 nucleotides from the 5' coding region for flavivirus core protein. The relative number of nucleotides from the 5' core protein coding region that will be required in the replicon for RNA replication will largely depend on the type of flavivirus used in the vector. For example when the replicon is derived from Kunjin virus it must contain at least 60 nucleotides of the 5' core protein coding region.

In one particular embodiment of the invention there is provided a gene expression system comprising:

a) a replicon of flavivirus origin which includes the nucleotide sequence for a flavivirus 5' untranslated region (UTR), at least a portion of the 5' coding region for flavivirus core protein, the nucleotide sequence coding for the flavivirus non-structural proteins, and part or all of the 3'-terminal sequence of a flavivirus 3'UTR, required for self-replication of flavivirus genomic material, which vector is adapted to receive at least a nucleotide sequence without disrupting its replication capabilities and which is unable to express at least part or all of a structural protein(s) region and or a protein(s) or part thereof required for packaging of a flavivirus genome into a virus-like particle; and b) at least a second vector that is capable of expressing flavivirus structural protein(s) and/or any other proteins required for packaging of the self-replicating expression vector into flavivirus viral particles which vector is engineered to prevent recombination with the self-replicating vector when in its presence.

According to the present invention, the replicon of flavivirus origin is adapted to receive at least a nucleotide sequence. Insertion of such a nucleotide sequence, into the replicon may be achieved at any point in the replicon that does not effect processing of flavivirus proteins. For example, heterologous genes may be inserted into the 3' UTR of the flavivirus replicon, within a structural gene or within the locality of deleted structural genes. Preferably, heterologous genes are inserted into structural genes or in place of deleted structural genes since such insertions generally produce higher levels of expression and generally do not affect replication efficiency of the replicon. If, however, the nucleotide sequence(s) are inserted into the 3'UTR they may be preceded by an internal ribosomal entry site (IRES) sequence. In an embodiment of the invention, the 3' UTR is used only for insertion of IRES-Neo (neomycin transferase) or IRES-pac (puromycin N-acetyl transferase) sequences. Such insertions allow the generation of stable cell lines persistently expressing foreign genes via antibiotic (eg Geneticin or puromycin) selection.

In another preferred embodiment of the invention there is provided a gene expression system comprising:

a) a replicon of flavivirus origin which includes a nucleotide sequence for a flavivirus 5'UTR, at least a portion of a 5' coding region for flavivirus core protein, a nucleotide sequence coding for a flavivirus non-structural proteins the complete or most of the 3'-terminal region of a flavivirus 3'UTR required for self-replication of the genomic material and the nucleotide coding sequence for flavivirus structural proteins, wherein (i) the vector is adapted to receive at least a nucleotide sequence without disrupting the replication capabilities of the vector, (ii) the nucleotide sequence is inserted into the vector in a manner which deactivates expression of at least a gene that would otherwise code for a flavivirus structural protein and (iii) the inserted nucleotide sequence does not encode for the structural protein sequence that it deactivates; and b) at least a second vector that is (i) capable of expressing the flavivirus structural protein(s) that is not expressed by the replicon and (ii) engineered to prevent recombination with the self-replicating vector when in its presence.

When the nucleotide sequence is inserted into the replicon it should be introduced into the vector in a manner which avoids a frame shift in the open reading frame of the vector coding sequence. This may be achieved by either adapting the foreign nucleotide sequence or the vector to ensure the reading frame of the vector coding sequence is maintained. In an alternative arrangement foreign nucleotide sequence can be inserted without preserving open reading frame of the vector if it is followed by a termination codon and an internal ribosomal entry site (IRES) sequence to ensure initiation of translation of the vector's nonstructural proteins.

A replicon which encodes flavivirus structural and non-structural proteins may be either RNA or DNA based provided it is capable of self-replication and encodes flavivirus structural and non-structural protein coding information. Where the replicon is an RNA sequence the flavivirus genome is first reverse transcribed into complementary DNA sequence and cloned into appropriate plasmid vector containing procaryotic (bacteriophage) DNA-dependent RNA polymerase promotor. The nucleotide sequence is then inserted into the resulting plasmid containing replicon complementary DNA sequence and the genomic sequence is then transcribed back into RNA prior to delivery to a host cell. Where the vector is DNA based the flavivirus genome is first reverse transcribed into complementary DNA sequence and cloned into appropriate plasmid vector containing eucaryotic expression promotor. A nucleotide sequence can then be inserted into the resulting plasmid containing replicon complementary DNA sequence which is then introduced into a host cell as plasmid DNA.

While the replicon will in most circumstances be prepared from a single strain of flavivirus it should be appreciated that in some circumstances nucleotide sequences from more than one flavivirus strain may be brought together in a single vector. Preferably the replicon is derived from the genomic sequence of a single flavivirus species. Most preferably the replicon is derived from a single flavivirus species (such as Kunjin virus (KUN)) and includes the entire or a substantial portion of the genome of that strain, the genome being modified in at least one of its structural proteins to accept a nucleotide sequence such that the insertion of the nucleotide sequence into the structural protein nucleotide sequence disrupts cod ing for part or all of the structural protein.

Nucleotide sequences that may be inserted into the replicon include, for example, parts of flavivirus or non-flavivirus cDNA gene sequences. Nucleotide sequence(s) that are inserted into the replicon must, however, disrupt the expression of at least a structural protein thus pre venting viral genome packaging. Desirably the inserted nucleotide sequence is a non-flavivirus nucleotide sequence (hereinafter referred to as a "heterologous nucleotide sequence"). The heterologous nucleotide sequence is not limited only to a sequence that encodes an amino acid sequence, but may also include sequences appropriate for promoting replication and or expression of a sequence that encodes an amino acid sequence.

Insertion of a heterologous nucleotide sequence into the replicon may occur at any point in a flavivirus structural protein(s) or in any region of the nucleotide sequence where such a protein would normally be expressed in the native flavivirus sequence had the protein not been deleted. In one embodiment of the invention the heterologous nucleotide sequence is inserted into at least one of the structural genes deactivating that gene. In another embodiment at least a structural gene is deleted from the vector and the deletion site is adapted to serve as the insertion site for heterologous genetic sequences. Most preferably, the nucleotide sequence is inserted into the locality from where at least a structural gene was deleted.

By positioning heterologous nucleotide sequences within the locality of one or more sites in the replicon that might otherwise code for structural genes in a native flavivirus, the replicon is unable to produce structural proteins for viral packaging.

To induce viral packaging the invention employs a second vector that is engineered to prevent recombination with the replicon. Preferably, the second vector is heterologous in origin to the origin of the replicon. Any non-flavivirus vector that is engineered to prevent recombination with the replicon may be employed in the expression system to deliver the flavivirus structural protein that is deactivated in the replicon. For example, if a KUN replicon is used as the self-replicating expression vector, then the second vector may be derived from a virus other than a flavivirus. For example, the second vector could be derived from an alphavirus such as SFV or SIN, or from DNA virus such as adenovirus, fowlpox virus, or vaccinia virus. Those of ordinary skill in the field will know other vectors that may be employed in this role. In a highly preferred form of the invention the replicon is derived from KUN while the second vector is derived from SFV to take account of the impossible recombination between KUN RNA and SFV RNA.

In an alternative embodiment of the invention the second vector may be a plasmid DNA expression vector. For example, highly efficient packaging may be achieved by inserting structural genes into CMV based DNA expression cassettes which are inserted into baculovirus expression vectors which provide very efficient delivery of the cassettes into mammalian cells (see for example Shoji et al, (1997) *J. Gen. Virol.*, 78: 2657–2664 and pBacMam-1 vector described on the Novagen homepage). In another example the second vector may be an inducible plasmid DNA expression vector (for example tetracycline inducible vector (Clontech)) allowing selection of packaging cell lines expressing KUN structural proteins in response to addition or removal of tetracycline in the incubation medium.

The present invention also provides a method for producing a stable cell line capable of persistently producing replicon RNA's, comprising the steps of:

(i) introducing into a cell a replicon of flavivirus origin which is adapted to receive at least a nucleotide sequence without disrupting its replication capabilities and which is unable to express at least part or all of a structural protein(s) region and or a protein(s) or part thereof required for packaging of a flavivirus genome into a virus-like particle; and (ii) culturing that cell line under conditions which permit cell growth and replication.

Conditions that permit cell growth and replication will be known to those of ordinary skill in the field. In particular the conditions will vary depending on the type of cell that is used in the method. To prepare such cell lines, the described vectors are preferably constructed in selectable form by inserting an IRES-Neo or IRES-pac cassette into the 3'UTR.

In another embodiment, the invention provides a method for producing a flavivirus like particles containing a replicon as herein described comprising the steps of:

(i) introducing into a cell a replicon of flavivirus origin which is adapted to receive at least a nucleotide sequence without disrupting its replication capabilities and which is unable to express at least part or all of a structural protein(s) region and or a protein(s) or part thereof required for packaging of a flavivirus genome into a virus-like particle;

(ii) introducing into a replicon containing cell a second vector that is capable of expressing flavivirus structural protein(s) and/or any other proteins required for packaging of the self-replicating expression vector into flavivirus viral particles which vector is engineered to prevent recombination with the self-replicating vector when in its presence; and (iii) harvesting virus like particles containing the replicon.

Preferably the replicon containing virus like particles prepared by this method are purified from cellular and viral proteins and nucleic acids that may cause an adverse immunological or physiological reaction when introduced into an animal. Methods for purifying such viral particles are known in the art. Most preferably the replicon containing virus like particles are 50%, 60%, 70%, 80%, 90%, 95% or 99% free of all contaminating material including cellular and viral proteins, lipids and nucleic acids.

In further embodiment, the invention provides a flavivirus like particles containing a flavivirus replicon that is adapted to receive at least a nucleotide sequence without disrupting its replication capabilities. Desirably the virus like particles are purified from cellular and viral nucleic acids and amino acid sequences that may cause an adverse immunological or physiological reaction when introduced into an animal. Such particles may be used as a therapeutic agent. A person of ordinary skill in the field will appreciate that the described virus particles can be used to deliver to a subject any nucleotide sequence that is inserted into the replicon. For example the replicon within the virus like particles may be employed to deliver to a cell a nucleotide sequence encoding one or more amino acid sequences which are capable of inducing, for example, a protective immune response to a subject.

In further embodiment, the invention provides a DNA based replicon of flavivirus origin that is adapted to receive at least a nucleotide sequence without disrupting its replication capabilities. The DNA based replicon may be introduced into a cell as a naked vector (i.e. flavivirus structural proteins do not surround it) or alternatively used for preparation of virus like particles containing encapsidated replicon RNA in accordance with the described method. Whether the DNA based replicon is prepared as a naked vector or in virus like particles it should be purified from cellular and viral nucleic acids and amino acid sequences that may cause an adverse immunological or physiological reaction in an animal prior to introduction into that animal. Such particles may be used as a therapeutic agent. A person of ordinary skill in the field will appreciate that the described virus particles can be used to deliver to a subject any nucleotide sequence that is inserted into the replicon. In a particularly preferred form of the invention the replicon is prepared in DNA form and is used for preparation of virus like particles containing encapsidated replicon RNA for delivery into a cell via infection.

DETAILED DESCRIPTION OF THE INVENTION

Although the present invention describes a means for producing proteins, the term "protein" should be understood to include within its scope parts of proteins such as peptide and polypeptide sequences.

In use, the replicon is introduced into a host cell where gene expression and hence protein production take place. Because the vector is capable of self-replication, multiple copies of the replicon will also be generated. This leads to an exponential increase in the number of replicons in the host cell as well as an exponential increase in the amount of protein that is produced.

Upon introduction of the second vector, containing the structural genes necessary to produce virus particles, structural proteins are produced. These proteins encapsulate the replicon therein forming a "pseudo" recombinant virus that is only capable of producing heterologous protein inside another cell. The pseudo-virus can not however replicate to produce new viral particles because the genes necessary for the production of the structural proteins are not provided in the replicon. Pseudo-virus stock will only be produced when co-transfection of the replicon and the vector bearing the structural genes occurs.

Some advantages associated with the use of the present invention include:
(1) The flavivrus expression system has relatively high level of protein expression in eukaryotic cell lines.
(2) The flavivirus expression system is capable of expressing proteins in a wide variety of mammalian cell lines and cell types.
(3) The replicons used in the flavivirus expression system produce a long-term non-cytopathic replication in host cells. There are no observable effects on the host's translation process. This feature of flavivirus replicons also allows selection of stable cell lines continuously expressing other genes using a replicon vector expressing a gene confirming resistance to an antibiotic (e.g. neomycin transferase (Neo), puromycin N-acetyltransferase (pac), etc.).
(4) The flavivirus expression system is an RNA system that does not permit integration of viral genomic material into a host's genomic sequence.

The replication of flaviviruses is quite different from other viruses. For example, flaviviruses differ from alphaviruses (such as SFV and SIN) by their genome structure (structural genes situated at the 5' end of the genome) and by the absence of synthesis of subgenomic RNA. Furthermore, there are no data to date on packaging of flavivirus RNA.

Substantial progress in the development of mammalian cell expression systems has been made in the last decade, and many aspects of these systems' features are well characterised. A detailed review of the state of the art of the production of foreign proteins in mammalian cells, including useful cell lines, protein expression-promoting sequences, marker genes, and gene amplification methods, is disclosed in Bendig, M., (1988) *Genetic Engineering* 7: 91–127.

It will be appreciated that any replicon derived from any flavivirus RNA, which is lacking at least a structural gene and which is adapted to receive at least a nucleotide sequence may be employed in the present invention. Preferably the replicon used in the invention should be adapted to include part or all of the following at least about the first 150 nucleotides of a flavivirus genome, at least about the last 60 nucleotides of E protein, substantially all of the nonstructural region, and part or all of the 3'UTR. Replication of a flavivirus genome is dependent on the genes in the nonstructural region of the genome being present during transcription and translation. Preferably any modification made to the nonstructural region should not interfere with the functional activity of the genes within the nonstructural region of the genome. In a highly preferred form of the invention, the replicon is derived from KUN and includes the first 157 nucleotides of the KUN genome, the last 66 nucleotides of E protein, the entire nonstructural region, and all of the 3'UTR.

Optimal flavivirus replicon design for transfection into eukaryotic cells might also include sequences inserted into the replicon such as: sequences to promote expression of the heterologous gene of interest, including appropriate transcription initiation, termination, and enhancer sequences; as well as sequences that enhance translation efficiency, such as the Kozak consensus sequence; internal ribosomal entry site (IRES) of picornaviruses; an alphavirus subgenomic 26S promoter to enhance expression of inserted genes if cotransfection with alphavirus replicon RNA is used.

Flavivirus replicon RNA can be produced in in vitro transcription reaction with DNA-dependent RNA polymerase from corresponding plasmid cDNA constructs incorporating a procaryotic (bacteriophage) promoter upstream of KUN genome sequence. Such replicon constructs are referred to as RNA-based replicon vectors. Resulting in vitro transcribed RNA can be delivered into the cell cytoplasm by RNA transfection followed by its self-amplification and translation resulting in expression of heterologous genes.

Alternatively, flavivirus replicon RNA can be produced in cells (in vivo) by the cellular transcription machinery after transfection of corresponding plasmid cDNA constructs incorporating a eucaryotic expression promoter upstream and transcription termination signal downstream of the KUN replicon sequence. These replicon constructs are referred to as DNA-based replicon vectors. Production of replicon RNA from these DNA-based vectors occurs in the nucleus of transfected cells by RNA polymerase II, followed by the transport of RNA into the cytoplasm where its amplification and translation takes place.

Finally, flavivirus replicon RNA produced in cells as a result of its self-amplification either after RNA transfection (RNA-based vector) or after plasmid DNA transfection (DNA-based vectors) can be packageed into the secreted virus-like particles by providing KUN structural proteins from a second vector. VLPs can then be used to deliver the encapsidated replicon RNA into cells by infection.

In one example of the invention the DNA-based replicon vector is derived from KUN virus and contains a eucaryotic promoter sequence (such as CMV or hybrid CMV enhancer-chicken β-actin promoter [CAG]) upstream of the KUN 5'UTR and a hepatitis delta virus ribozyme sequence followed by an SV40, bovine growth hormone, or rabbit β-globin transcription terminator sequences downstream of the KUN 3'UTR. Transfection of the resulting plasmid DNA in cells will ensure production of a KUN replicon RNA transcript with the authentic 5'-end by cellular RNA polymerase II and with the authentic 3'-end cleaved by hepatitis delta virus ribozyme, which is preferred for its efficient replication.

It will be appreciated that the nucleotide sequence inserted into the replicon may encode part or all of any natural or recombinant protein except for the structural protein sequence into which or in place of which the nucleotide sequence is inserted. For example, the nucleotide sequence may encode a single polypeptide sequence or a plurality of sequences linked together in such a way that each of the sequences retains their identity when expressed as an amino acid sequence. Where the nucleotide sequence encodes a plurality of peptides, the peptides should be linked together in such a way that each retains its identity when expressed. Such polypeptides may be produced as a fusion protein or engineered in such a manner to result in separate polypeptide or peptide sequences.

Where the vector is used to deliver nucleotide sequences to a host cell to enable host cell expression of immunogenic polypeptides, the nucleotide sequence may encode one or more immunogenic polypeptides in association with a range of epitopes which contribute to T-cell activity. In such circumstances the heterologous nucleotide sequence preferably encodes epitopes capable of eliciting either a T helper cell response or a cytotoxic T-cell (CTL) response or both.

The replicon described herein may also be engineered to express multiple nucleotide sequences allowing co-expression of several proteins such as a plurality of antigens together with cytokines or other immunomodulators to enhance the generation of an immune response. Such a replicon might be particularly useful for example in the production of various proteins at the same time or in gene therapy applications.

By way of example only the nucleotide sequence may encode the cDNA sequence of one or more of the following: malarial surface antigens; beta-galactosidase; any major antigenic viral antigen eg Haemagglutinin from influenza virus or a human immunodeficiency virus (HIV) protein such as HIV gp 120 and HIV gag protein or part thereof: any eukaryotic polypeptide such as, for example, a mammalian polypeptide such as an enzyme, e.g. chymosin or gastric lipase; an enzyme inhibitor, e.g. tissue inhibitor of metalloproteinase (TIMP): a hormone, e.g. growth hormone, a lymphokine, e.g. an interferon; a cytokine, e.g an interleukin (eg IL-2, IL-4, IL-6 etc); a chemokine eg macrophage inflammatory protein-2; a plasminogen activator, e.g. tissue plasminogen activator (tPA) or prourokinase; or a natural, modified or chimeric immunoglobulin or a fragment thereof including chimeric immunoglobulins having dual activity such as antibody-enzyme or antibody-toxin chimeras.

The nucleotide sequence may also code for one or more amino acid sequences that serve to enhance the effect of the protein being expressed. For example, ubiquitination of viral proteins expressed from DNA vectors results in enhancement of cytotoxic T-lymphocyte induction and antiviral protection after immunization. Thus, in a preferred embodiment of the invention the replicon may encode ubiquitin in association with the protein to be expressed thus targeting the resulting fusion protein to proteosomes for efficient processing and uptake by the MHC class I complexes.

In frame fusion of proteins other than flavivirus replicon encoded proteins to the C-terminus of ubiquitin also results in the efficient cleavage of such fusion protein after the last C-terminal residue of ubiquitin thus releasing free protein of interest. Preferably a ubiquitin sequence is inserted into the replicon vector. By way of example only the ubiquitin sequence is preferably inserted either prior to the 5' end of the heterologous genetic sequence or at the 3' end of the heterologous genetic sequence.

The second vector that contains the flavivirus structural gene(s) should be engineered to prevent recombination with the self-replicating expression vector. One means for achieving this end is to prepare the second vector from genetic material that is heterologous in origin to the origin of the self-replicating expression vector. For example, the second vector might be prepared from SFV when the replicon is prepared from KUN virus.

To optimise expression of the flavivirus structural genes, the second vector might include such sequences as: sequences to promote expression of the genes of interest, including appropriate transcription initiation, termination, and enhancer sequences: as well as sequences that enhance translation efficiency, such as the Kozak consensus sequence. Preferably, the second vector contains separate regulatory elements associated with each of the different structural genes expressed by the vector. Most preferably, the flavivirus C gene and the prME genes are placed under the control of separate regulatory elements in the vector.

The processing of flavivirus structural proteins during virus replication in cells is complex and requires a number of post-translational cleavages by host and viral proteases. Numerous in vitro and in vivo studies on processing of the C-prM region have established two cleavage events: cleavage at a dibasic cleavage site by viral NS2B-NS3 protease generating the carboxy terminus of mature virion C protein, which appears to be a prerequisite for the efficient cleavage at the $NH_2$ terminus of prM by cellular signalase. While viral proteases are expressed by the replicon during expression of the genes forming the nonstructural region of a flavivirus, it will be appreciated that the second vector may also be adapted to include genes encoding viral NS2B-NS3 protease.

Further C-prM-E genes can be expressed as a single cassette only if C and prM genes separated by a self-cleaved peptide like for example 2A autoprotease of foot-and-mouth disease virus in order to ensure proper processing of C-pM region in the absence of KUN virus encoded NS2B-NS3 protease.

The present invention also provides stable cell lines capable of persistently producing replicon RNAs. To prepare such cell lines, the described vectors are preferably constructed in selectable form by inserting an IRES-Neo or IRES-pac cassette into the 3'UTR.

Host cell lines contemplated to be useful in the method of the invention include any eukaryotic cell lines that can be immortalised, ie., are viable for multiple passages, (eg., greater than 50 generations), without significant reduction in growth rate or protein production. Useful cell line should also be easy to transfect, be capable of stably maintaining foreign RNA with an unarranged sequence, and have the necessary cellular components for efficient transcription, translation, post-translation modification, and secretion of the protein. Currently preferred cells are those having simple media component requirements, and which can be adapted for suspension culturing. Most preferred are mammalian cell lines that can be adapted to growth in low serum or serum-free medium. Representative host cell lines include BHK (baby hamster kidney), VERO, C6-36, COS, CHO (Chinese hamster ovary), myeloma, HeLa, fibroblast, embryonic and various tissue cells, eg., kidney, liver, lung and the like and the like. Desirably a cell line is selected from one of the following: BHK21 (hamster), SK6 (swine), VERO (monkey), L292 (mouse), HeLa (human), HEK (human), 2fTGH cells, HepG2 (human). Useful cells can be obtained from the American Type Culture Collection (ATCC), Rockville, Md. or from the European Collection of Animal Cell Cultures, Porton Down, Salisbury SP40JG, U.K.

With respect to the transfection process used in the practice of the invention, all means for introducing nucleic acids into a cell are contemplated including, without limitation, CaPO.sub.4 co-precipitation, electroporation, DEAE-dextran mediated uptake, protoplast fusion, microinjection and lipofusion. Moreover, the invention contemplates either simultaneous or sequential transfection of the host cell with vectors containing the RNA sequences. In one preferred embodiment, host cells are sequentially transfected with at least two unlinked vectors, one of which contains flavivirus replicon expressing heterologous gene, and the other of which contains the structural genes.

The present invention also provides virus like particles containing flavivirus replicons and a method for producing such particles. It will be appreciated by those skill in the art that virus like particles that contain flavivirus derived replicons can be used to deliver any nucleotide sequence to a cell. Further, the replicons may be of either DNA or RNA in structure. One particular use for such particles is to deliver nucleotide sequences coding for polypeptides that stimulate an immune response. Such particles may be employed as a therapeutic or in circumstances where the nucleotide sequence encodes peptides that are capable of eliciting a protective immune response they may be used as a vaccine. Another use for such particles is to introduce into a subject a nucleotide sequence coding for a protein that is either deficient or is being produced in insufficient amounts in a cell.

The replicon containing flavivirus like particles that contain nucleotide coding sequence for immunogenic polypeptide(s) as active ingredients may be prepared as injectables, either as liquid solutions or suspensions, solid forms suitable for solution in, or suspension in, liquid prior to injection may also be prepared. The flavivirus replicon therapeutic(s) may also be mixed with excipients that are pharmaceutically acceptable and compatible with the replicon encapsulated viral particle. Suitable excipients are, for example, water, saline, dextrose glycerol, ethanol, or the like and combinations thereof. In addition, if desired, the therapeutic may contain minor amounts of auxiliary substances such as wetting or emulsifying agents, pH buffering agents, and/or adjuvant which enhance the effectiveness of the therapeutic.

The replicon containing flavivirus like particles may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10%–95% of virus like particles, preferably 25–70%.

The flavivirus like particles may be formulated into the vaccine as neutral or salt forms. Pharmaceutically acceptable salts include the acid addition salts (formed with free amino groups of the peptide) and which are formed with inorganic acids such an, for example, hydrochloric or phosphoric acids, or such organic acids such as acetic, oxalic, tartaric, maleic, and the like. Salts formed with the free carboxyl groups may also be derived from in-organic bases such as, for example, sodium, potassium, ammonium, calcium, or ferric hydroxides, and such organic bases as isopropylamins, trimethylamine, 2-ethylamino ethanol, histidino, procaine, and the like.

The flavivirus like particles may be administered in a manner compatible with the dosage formulation and in such amount as will be prophylactically and/or therapeutically effective. The dose of viral particles to be administered depends on the subject to be treated, the type of nucleotide sequence that is being administered and the type of expression efficiency of that sequence and in the case where the nucleotide sequence encodes immunogenic peptide/polypeptides the degree of protection desired. Precise amounts of active ingredient required to be administered may depend on the judgment of the practitioner and may be peculiar to each subject.

The flavivirus like particles may be given to a subject in a single delivery schedule, or preferably in a multiple delivery schedule. A multiple delivery schedule is one in which a primary course of delivery may be with 1–10 separate doses, followed by other doses given at subsequent time intervals required to maintain and or re-enforce the effect sought and if needed, a subsequent dose(s) after several months. The delivery regimen will also, at least in part, be determined by the need of the individual and be dependent upon the judgment of the practitioner.

BRIEF DESCRIPTION OF THE DRAWINGS

Further features of the present invention are more fully described in the following Figures and Examples. In the figures:

FIG. 2 illustrates a schematic representation of the recombinant SFV constructs. The solid line in all constructs represents the segment of the SFV replicon genome flanking the multiple cloning site, open boxes show the inserted KUN structural genes C, prM, and E as indicated, 26S shows the position of the subgenomic SFV promoter, the filled and partially filled boxes in the KUN prM and E genes represent hydrophobic signal and anchor sequences, respectively. Capital letters in the nucleotide sequences show authentic KUN nucleotides, small letters show nucleotides derived from the pSFV1 vector or encoded in the primers used for PCR amplification of KUN genes. Bold and italicised letters show initiation (ATG) and termination (taa, tag) codons. Numbers with arrows represent amino acid positions in the KUN polyprotein. Msc, Sma, Spe, Bam, and Bgl represent specific restriction sites. Asterisks indicate that these restriction sites were destroyed during the cloning procedure.

FIG. 4 illustrates expression of KUN prME genes by recombinant SFV replicon. A) IF analysis of SFV-prME and SFV1 transfected BHK21 cells at 18 h after transfection using KUN monoclonal anti-E antibodies. (B) and (C) show the results of pulse-chase labelling and radioimmunoprecipitation analysis with KUN monoclonal anti-E antibodies, respectively, of SFV-prME transfected BHK21 cells, where CF (culture fluid) and C (cells) represent samples collected during chase periods. Lanes 1 to 9 in (B) and (C) represent the same samples either directly electrophoresed in 12.5% SDS-polyacrylamide gel (B), or radioimmunoprecipitated with anti-E antibodies followed by electrophoresis in a 12.5% SDS-polyacrylamide gel (C). Lanes 2 and 9 show samples collected after a 4 h-chase period from culture fluid and cells, respectively, after transfection with the control SFV1 RNA. Lanes 3, 4, and 5 show culture fluid samples collected at 1 h, 4 h, and 6 h of chase periods, respectively, and lanes 6, 7, and 8 show the corresponding chase samples from the cells. In (B) 10 μl of total 700 μl of culture fluid and 5 μl of total 300 μl of cell lysates samples were used for electrophoresis. In (C) 10 μl of total 30 μl of immunoprecipitate prepared either from 150 μl of the cell lysate or from 350 μl of the culture fluid were used for electrophoresis. The exposure time of the dried gel for cell lysates was 1 day, and 5 days for culture fluids. Dots in lane 1 of (B) and (C) indicate KUN proteins in the radiolabeled KUN cell lysates, as in FIG. 2B. Numbers represent molecular weights in the low range pre-stained Bio-Rad protein standards.

FIG. 5 illustrates expression of all three KUN structural proteins by the recombinant SFV-prME-C replicon. A) Double IF analysis of the same field in BHK21 cells at 18 h after transfection with SFV-prME RNA using KUN anti-C (panel 1) and anti-E (panel 2) antibodies, with Texas Red (TR) and FITC conjugated secondary antibodies, respectively. In (B) and (C), cells at 18 h after transfection with SFV-prME-C RNA were pulsed with $^{35}$S-methionine/cysteine for 1 h; subsequently, 300 μl (from total of 600 μl) of cell lysates ("C" in [B] and in [C]) and 1 ml (from total of 2 ml) of culture fluids ("CF" in [B]) collected at different chase intervals (1 h, 6 h, and 9 h), were immunoprecipitated either with KUN monoclonal anti-E antibodies (B), or with KUN anti-C antibodies (C). Ten μl (from total of 30 μl) of immunoprecipitated samples were electrophoresed in 12.5% (B) and 15% (C)SOS-polyacrylamide gels. Dots in (B) indicate KUN proteins in the labelled KUN cell lysates as in FIG. 2B. Dots in (C) represent KUN proteins prM. NS2A. C, and NS4A/NS2B (from top to bottom) in the radiolabeled KUN infected cell lysate. Numbers represent molecular weights of the low range pre-stained Bio-Rad protein standards.

FIG. 6 illustrates packaging of KUN replicon RNA by KUN structural proteins expressed from the recombinant SFV replicons. (A) IF analysis with KUN anti-NS3 antibodies of BHK21 cells infected with the culture fluid collected from BHK21 cells at 26 h after transfection first with C20DXrep RNA and 26 h later with SFV-prME-C RNA (panel 1), or with SFV-prME and SFV-C RNAs (panel 2), or with SFV-prME RNA (panel 3). (B) and (C) show Northern blot analysis of RNAs isolated from BHK21 cells infected as described in (A), using labelled KUN-specific (B) and SFV-specific (C) cDNA probes. Lane 1 in (B) and lane 2 in (C) correspond to the cells in panel 1 in (A). Lane 2 in (B) and lane 3 in (C) correspond to the cells in panel 2 in (A). Lane 1 in (C) represents in vitro synthesized SFV-prME-C RNA. Arrows in (B) and (C) indicate the positions of RNAs of about 8.8 kb for KUN replicon RNA and about 10.8 kb for SFV-prME-C RNA determined relative to migration in the same gel of ethidium bromide-stained λ DNA digested with BstEII (New England Biolab).

FIG. 9. Sedimentation and electron microscopy analyses of KUN replicon and virion particles. (A) Sedimentation profiles of virions and replicon particles in parallel sucrose density gradients. Particles were collected from culture fluids of BHK cells either at 35 h after sequential transfections with C20DXrep and SFV-prME-C107 RNAs, or at 24 h after infection with KUN virus, and were concentrated by ultracentrifugation as described in Materials and Methods. The pelleted particles were resuspended in 300 μl of PBS- 0.1% BSA overnight at 4° C. and clarified by centrifugation at 16,000 g in the microcentrifuge for 10 min. The supernatant was overlaid on the top of a 12 ml 5–25% sucrose density gradient which was centrifuged at 38,000 rpm for 70 min at 20° C. in an SW41 rotor, 0.5 ml fractions were collected from the bottom of the gradient and diluted 1:2 (replicon particles) or 1:100 (KUN virions) for infectivity assays by IF on cover slip cultures of BHK cells at 24 h (replicon particles) or at 18 h (KUN virions) after infection, using anti-E antibodies; titers of infectious particles were determined as described earlier (see. (B) Electron micrographs of virions (left panel) and encapsidated replicon particles (right panel) stained with uranyl acetate. Fractions 5–7 of replicon particles in (A), and fractions 2–4 of KUN virions, were pooled and incubated with 1/20 dilution of anti-E antibodies for 1 h at 20° C., followed by 2 h incubation at 4° C. with constant rotation. Particles were then again concentrated by ultracentrifugation as described above, and pellets were resuspended in 175 $\mu$l of PBS-0.1% BSA overnight at 4° C. Resuspended particles were then sonicated in the Transsonic 700/h sonicating water bath (CAMLAB, Germany) for 1 min and pelleted onto a carbon coated formvar grid by centrifugation in an 18° fixed angle A-100 rotor in a Beckman Airfuge for 1 h at 80,000 rpm. Grids were stained with 4% uranyl acetate and particles were visualized by electron microscopy. The bar represents 200 nm.

FIG. 14. Packaging of the recombinant KUN replicon RNAs. (A) GFP fluorescence and IF analysis of BHK21 and Vero cells at 35 h after infection with culture fluid collected from BHK21 cells sequentially transfected with recombinant KUN replicon RNAs and SFV-prME-C105 RNA using corresponding antibodies as indicated. Time intervals between transfections were 30 h for C20DX/GFP/2Arep, 34 h for C20DX/VSV-G/2Arep, and 42 h for C20DX/hcv-NS3/2Arep RNAs. Time intervals for harvesting culture fluid after second transfections with SFV-prME-C105 RNA were 24 h, 37 h, and 38 h, respectively. (B) Autoradiogram of the CAT assay of the lysates from BHK21 cells (BHK mock) or BHK21 cells at 30 h after infection with the culture fluid collected from BHK21 cells at 26 h after transfection with C20DX/CAT/2Arep RNA and 42 h after transfection with SFV-prME-C105 RNA. CAT assay in was performed as described the examples.

FIG. 16. (A) Schematic representation of KUN replicon expression vector containing ubiquitin gene (C20DXUb2Arep). Ub shows ubiquitin gene, all the other abbreviations as in FIG. 10. (B) IF analysis of BHK cells at 24 h after transfection with C20DXrep and C20DXUb2Arep RNAs using anti-NS3 antibodies.

FIG. 17. (A). illustrates the construction of full-length C20DXUb2A_HDVrep vector (FIG. 17A). (B) illustrates efficient replication of C20DXUb2A_HDVrep RNA in ~100% BHK21 cells compared to ~60% positive cells obtained after transfection with the same amounts of parental C20DXUb2Arep RNA (FIG. 17B).

FIG. 18. (A). illustrates the construction of DNA-based pKUNRep1 vector (FIG. 18A). (B) shows successful detection of expression of the KUN NS3 protein (indicator of the replicating KUN replicon RNA) at 42 h post transfection with pKUNRep1 plasmid DNA (FIG. 18B).

BEST MODE(S) FOR CARRYING OUT THE INVENTION

Figure 1:
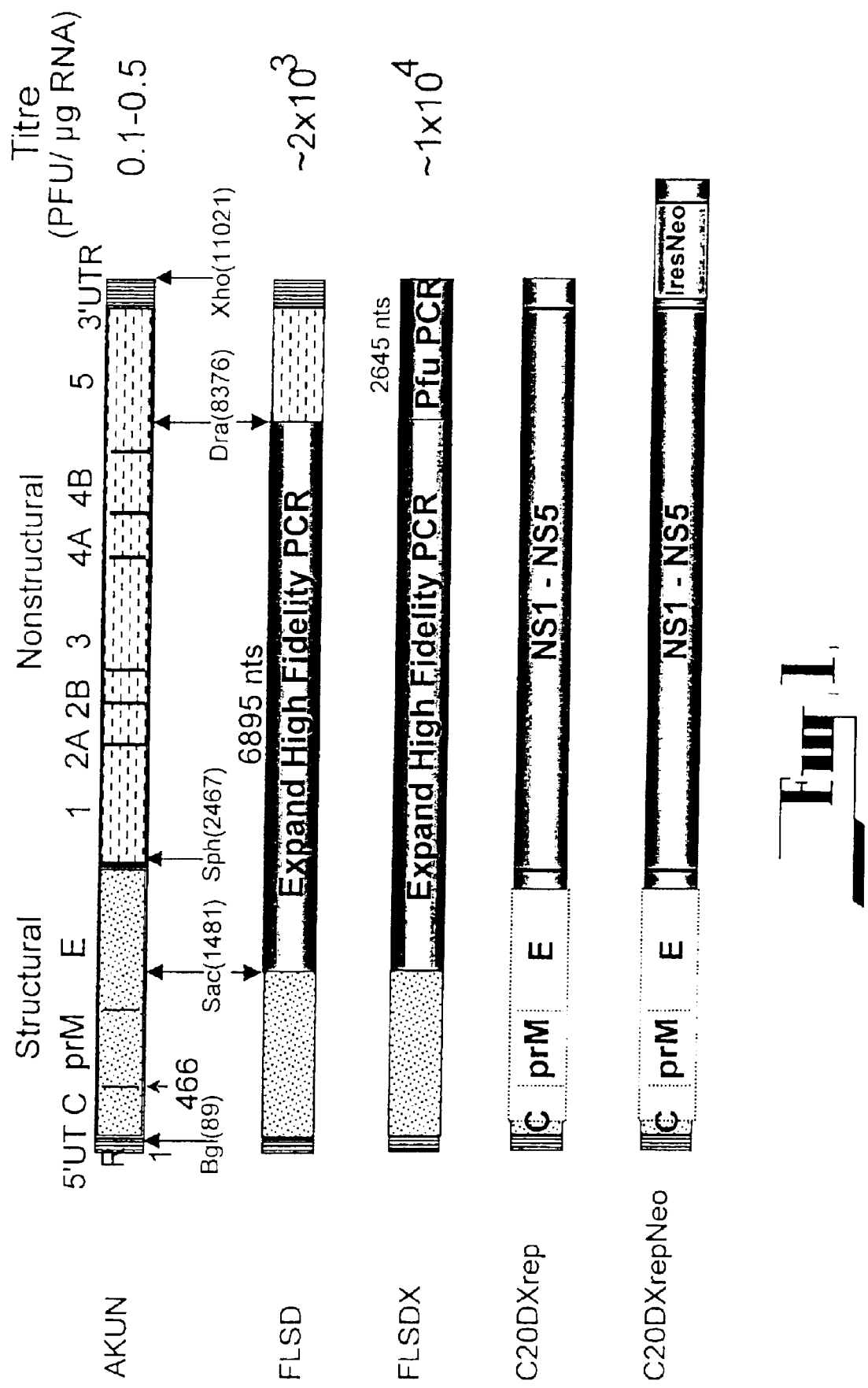
FIG. 1: illustrates the construction and specific infectivity of the full-length KUN cDNA clones, and the structure of KUN replicon RNAs. Schematic representations of the full-length and deleted (replicon) constructs show consecutive substitutions of the cDNA fragments in AKUN clone (textured boxes) with analogous fragments obtained by RT-PCR from KUN virion RNA (shaded boxes). PFU titers on the right hand side of the figure represent an average (from three experiments) obtained after electroporation of the transcribed RNAs into BHK21 cells and determined by plaque assay; the titer of purified wild type KUN RNA was $\sim 10^5$–$10^6$ PFU/µg RNA. Bgl(89), Sac(1481), Sph(2467), Dra(8376), Xho(11021) show restriction enzyme sites used in replacement cloning with the numbers in brackets representing nucleotide numbers in the KUN sequence. An Expand High Fidelity PCR kit (Boehringer Mannheim) was used to obtain the indicated cDNA fragment of 6895 nucleotides in the FLSD and FLSDX constructs, and "Pfu PCR" in FLSDX indicates that this cDNA fragment of 2645 nucleotides was obtained using Pfu DNA polymerase (Stratagene). C20DXrep and C20DXrepNeo constructs were prepared as described below in Example 1 (C20DXrep) and in Example 4 (C20DXrepNeo). Open boxes represent the deleted part of the genome; Ires— internal ribosomal entry site of encephalomyelitis virus RNA; Neo—neomycin transferase gene.

Further features of the present invention are more fully described in the following Examples. It is to be understood that the following Examples are included solely for the purposes of exemplifying the invention, and should not be understood in any way as a restriction on the broad description as set out above.

EXAMPLE 1

Cells.

BHK21 cells were grown in Dulbecco's modification of minimal essential medium (Gibco BRL) supplemented with 10% foetal bovine serum at 37° C. in a $CO_2$ incubator.

Construction of the Replicons and Vectors.

(i) C20rep: All deletion constructs were prepared from the cDNA clones used in the construction of the plasmid pAKUN for generation of the infectious KUN RNA (Khromykh and Westaway, J. Virol., 1994, 68:4580–4588) by PCR-directed mutagenesis using appropriate primers and conventional cloning. dME cDNA and its derivatives were deleted from nucleotides 417 to 2404, which represent loss of the signal sequence at the carboxy terminus of C now reduced to 107 amino acids, deletion of prM and E, with the open reading frame resumed at codon 479 in E, preceding the signal sequence for NS1. C20 rep and C2rep cDNAs represent progressive in frame deletions in coding sequence of C leaving only 20 or 2 amino acids of C, respectively, with the open reading frame continued at codon 479 in E, as in dME.

(ii) FLSDX: All RT reactions were performed with Superscript II RNase H-reverse transcriptase (Gibco BRL) essentially as described by the manufacturer using 100–200 ng of purified KUN virion RNA, or 1 μg of total cell RNA and appropriate primers. PCR amplification after RT of a 6895 bp DNA fragment was performed with the Expand High Fidelity PCR kit (Boehringer Mannheim) using 1/25 volume of RT reaction and appropriate primers as follows. The PCR reaction mixture (50 μl) containing all necessary components except the enzyme mixture (3 parts of Taq polymerasse and 1 part of Pwo polymerase) was preheated at 95° C. for 5 min, then the enzyme mixture was added and the following cycles were performed: 10 cycles of 95° C. for 15 sec and 72° C. for 6 min, followed by 6 cycles of 95° C. for 15 sec and 72° C. for 6 min with an automatic increase of extension time at 72° C. for 20 sec in each following cycle. All PCR reactions with Pfu DNA polymerasse (Stratagene) were performed essentially as described by the manufacturer using 1/25–1/10 volumes of RT reactions and appropriate primers.

All plasmids shown in FIG. 1 were obtained from the previously described stable KUN full-length cDNA clone pAKUN (Khromykh and Westaway, J. Virol., 1994, 68:4580–4588) by substitution of the original cDNA fragments with those obtained by RT and PCR amplification of purified KUN RNA using existing unique restriction sites which were also incorporated into the primers for PCR amplification.

Initially the $SacII^{1481}$-$DraIII^{8376}$ (6895 bp) fragment in pAKUN clone (FIG. 1) was replaced with the fragment amplified using Expand High Fidelity PCR kit from the cDNA obtained by reverse transcription of purified KUN virion RNA using appropriate primers. RNA transcribed from the resulting cDNA clone (FLSD) had a specific infectivity of $\sim 2\times 10^3$ PFU per 1 μg, compared to only 1–5 PFU per 10 μg for AKUN RNA (FIG. 1). We then commenced replacing the rest of the genome using PCR with the high fidelity Pfu DNA polymerase (Stratagene). Thus a 2645 nts $DraIII^{8376}$-$XhoI^{11021}$ fragment covering most of the NS5 gene and the entire 3'UTR was inserted in FLSD cDNA to produce FLSDX (FIG. 1), resulting in a total $10^4$–$10^5$-fold improvement of the original specific infectivity, now equivalent to $\sim 10^4$ PFU/μg RNA (FIG. 1). Further replacement of the 1392 nts $BglII^{89}$-$SacII^{1481}$ fragment covering C, prM and part of E sequence did not noticeably improve the specific infectivity of the resulting FLBSDX RNA (data not shown). The most infectious FLSDX clone was therefore used in all further experiments.

(iii) C20DXrep. KUN replicon cDNA construct C20DXrep was constructed from described above C20rep by replacing an $SphI^{2467}$-$XhoI^{11021}$ fragment representing the sequence coding for the entire nonstructural region and the 3'UTR with the corresponding fragment from a stable full-length KUN cDNA clone FLSDX. Transfection of BHK cells with 5–10 μg of C20DXrep RNA resulted in detection of –80% replicon-positive cells compare to only ~10% positive after transfection with the same amount of C20rep RNA.

(iv) SFV-C. An SFV replicon construct expressing KUN core (C) gene was obtained by cloning of the BglII-BamHI fragment, representing the sequence of the last 7 nucleotides of the KUN 5'UTR and the sequence coding for the first 107 of the 123 amino acids of KUN C protein, from the plasmid pCINeoC107 (Khromykh, A. A. and E. G. Westaway. Arch. Virol., 1996, 141:685–699) into the BamHI site of the SFV replicon expression vector pSFV1 (Gibco BRL; FIG. 2).

Figure 2:
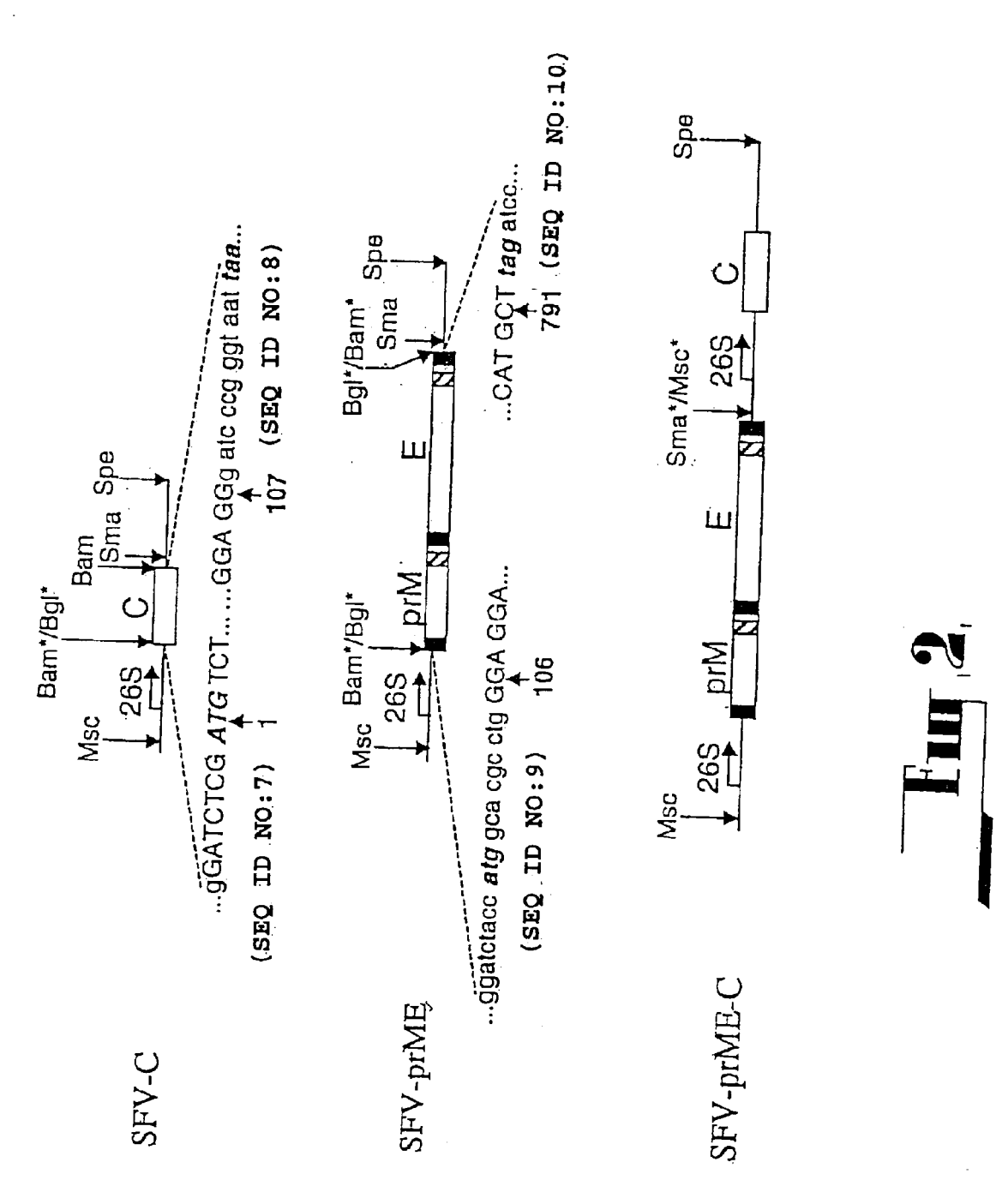

(v) SFV-prME. KUN prME sequence was PCR amplified from another highly efficient full-length KUN cDNA clone FLBSDX modified from FLSDX (which will be described elsewhere), using appropriate primers with incorporated BglII sites. The amplified fragment was digested with BglII and cloned into the BamHI site of the SFV replicon expression vector pSFV1 to obtain the SFV-prME construct (FIG. 2).

(vi) SFV-prME-C. SFV replicon construct expressing both KUN prME and KUN C genes was obtained by cloning a MscI-SpeI fragment from the SFV-C plasmid containing the SFV 26S subgenomic promoter, KUN C sequence and SFV 3'UTR into the SFV-prME vector digested with SmaI and SpeI (FIG. 2). Thus the final double subgenomic construct SFV-prME-C should produce SFV replicon RNA which upon transfection into BHK cells will direct synthesis of two subgenomic RNAs expressing KUN prME and KUN C genes.

RNA Transcription and Transfection.

RNA transcripts were prepared from C20DXrep plasmid DNA linearized with XhoI, and from SFV plasmids linearised with SpeI using SP6 RNA polymerase. Electroporation of RNAs into BHK21 cells was performed. Briefly, 10–20 µg of in vitro transcribed RNAs were electroporated into 2×10$^6$ BHK21 cells in 400 µl in a 0.2-cm cuvette (Bio-Rad) using the Bio-Rad Gene Pulser apparatus.

Immunofluorescence Analysis.

Replication of KUN replicon RNA C20DXrep after initial electroporation, and after infection of BHK cells in packaging experiments, was monitored by immunofluorescence (IF) analysis with antibodies to KUN NS3 protein. Expression of KUN E protein after electroporation with SFV-prME and SFV-prME-C RNAs was detected by IF with a cocktail of mouse monoclonal antibodies to KUN E protein. These antibodies designated 3.91D, 10A1, and 3.67G were generously provided by Roy Hall, University of Queensland, Brisbane, Australia. All three antibodies were mixed in equal amounts and a 1/10 dilution of this mixture was used in IF analysis. Expression and nuclear localisation of KUN C protein after electroporation with SFV-C and SFV-prME-C RNAs was monitored by IF analysis with rabbit polyclonal antibodies to KUN C protein.

Metabolic Labeling and Radioimmunoprecipitation Analysis.

Metabolic labeling with $^{35}$S-methionine/cysteine of electroporated BHK cells was performed essentially as described in the SFV Gene Expression System Manual with some minor modifications. Briefly, cells at 18 h after the electroporation with SFV RNAs (with or without prior electroporation with KUN replicon RNA), were pulse labeled with $^{35}$S-methionine/cysteine for 4 h, or for 1–2 h followed by different periods of incubation (chase) in medium with an excess of unlabeled methionine/cysteine. Cell culture fluid was collected for analysis of secreted proteins by electrophoresis and radioimmunoprecipitation (RIP). Labeled cells were lysed in buffer containing 1% Nonidet P40 (NP40), 50 mM Tris-HCl (pH 7.6), 150 mM NaCl, and 2 mM EDTA, the nuclei removed by low speed centrifugation and the lysate supernatant was used for parallel analysis with the culture fluid.

For RIP analysis, labeled cell culture fluids were first filtered through 0.45 µm filter (Sartorius AG, Gottingen, Germany) and digested with RNase A (20 µg per ml) for 30 min at 37° C. to ensure the removal of membrane particulate material and naked RNA. Filtered and RNase treated culture fluids, or untreated cell lysates, were then mixed with 1/20 volume of the pooled anti-E monoclonal antibodies (see above) or with rabbit anti-C antibodies, and incubated overnight at 4° C. with constant rotation in microcentrifuge tubes. Protein A-Sepharose beads were then added to a final concentration of about 1%, and incubation was continued for another 1 h at 4° C. After three washes with RIPA buffer (50 mM Tris-HCl, pH 7.6; 150 mM NaCl; 1% NP40; 0.5% deoxycholic acid sodium salt [DOC]; 0.1% sodium dodecyl sulfate [SDS]) and one wash with phosphate buffered saline (PBS), beads were resuspended in the SDS-gel sample buffer, boiled for 5 min and subjected to electrophoresis in an SDS-polyacrylamide gel. After electrophoresis gels were dried and exposed to X-ray film.

Northern Blot Hybridisation.

Figure 7:
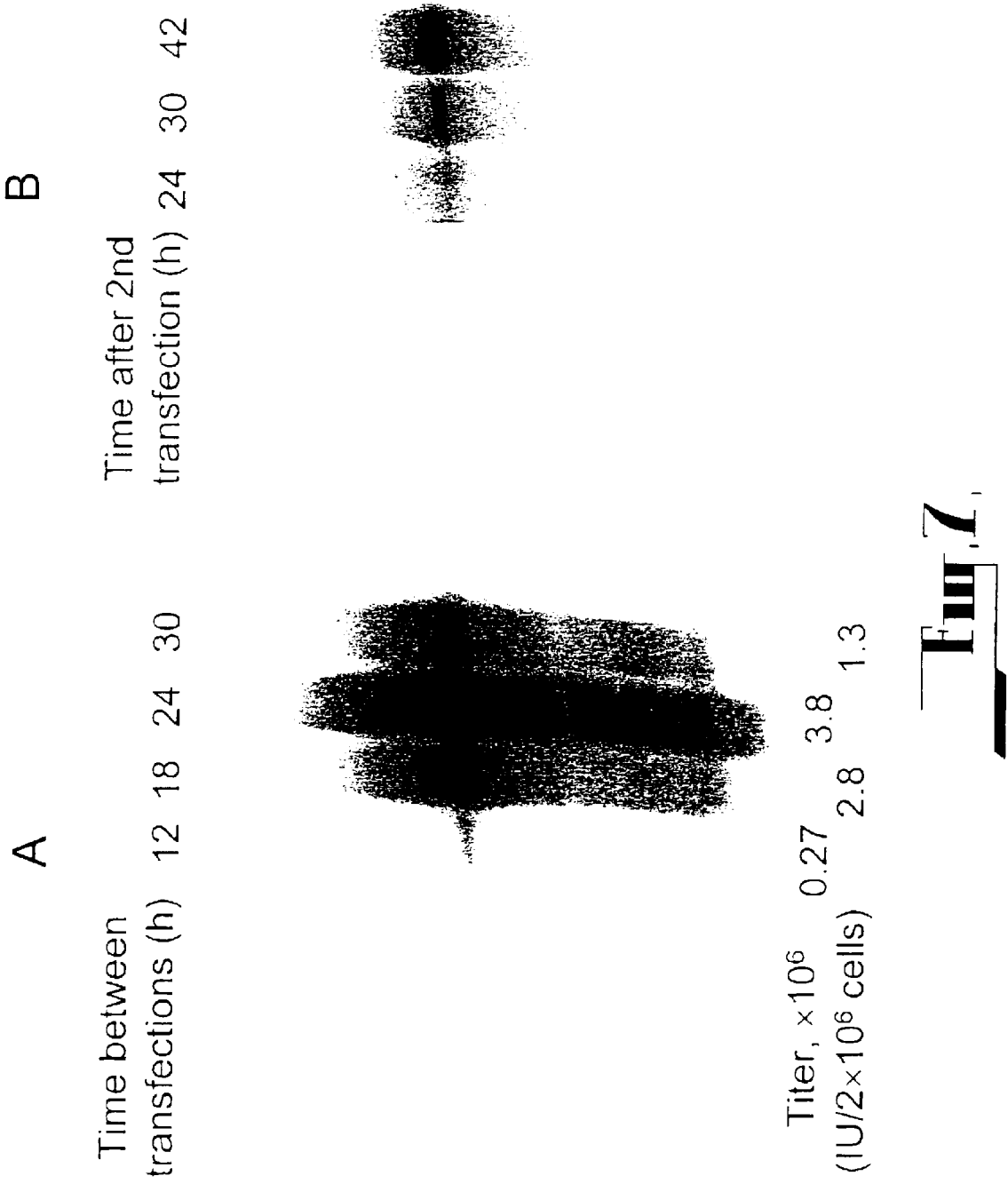
FIG. 7 illustrates optimisation of conditions for packaging of KUN replicon RNA. Northern blot analysis of BHK21 cells infected with filtered and RNase-treated culture fluid samples. In (A), samples were collected at a fixed time (24 h) after second transfection (with SFV-prME-C RNA) and using different time intervals as shown between transfections of C20DXrep and SFV-prME-C RNAs. In (B), samples were collected at different times as shown after the second transfection (with SFV-prME-C RNA) which occurs at a fixed time (30 h) after the first transfection (with C20DXrep RNA). The probe in both (A) and (B) was a radiolabeled cDNA fragment representing the last 761 nucleotides of the KUN genome. Titers in (A) shown under the lanes in the Northern blot represent the amounts of infectious units (IU) contained in the corresponding samples of culture fluids used for infections and determined by IF analysis with anti-NS3 antibodies and counting of IF positive cells.

Five µg total RNA, isolated using Trizol reagent (Gibco BRL) from BHK21 cells infected with culture fluid collected from cells doubly transfected with C20DXrep RNA and SFV RNAs expressing KUN structural proteins, was electrophoresed for Northern blotting. The hybridisation probes were [$^{32}$P]-labelled cDNA fragments representing the 3'-terminal 761 nucleotides of the KUN genome including the 3'UTR region (see FIG. 6B and FIG. 7), and 446 nucleotides of the SFV NSP2 region (see FIG. 6C).

Expression of KUN C Gene by the Recombinant SFV-C Replicon.

For the expression of KUN C gene in the pSFV1 vector the BglII-BamHI fragment from plasmid pCINeoC107 was subcloned into the BamHI site of pSFV1 (FIG. 2). This fragment represents the sequence coding for the first 107 amino acids of KUN C protein, equivalent to the mature form of C, from which the carboxy terminal hydrophobic sequence has been removed. The SFV-C construct also contains a native KUN initiation codon with an extra 7 nucleotides of the KUN 5'UTR derived from the pCINeoC107 plasmid and four extra codons at the carboxy-terminus derived from the SFV vector sequence (FIG. 2).

Figures 3A, 3B:
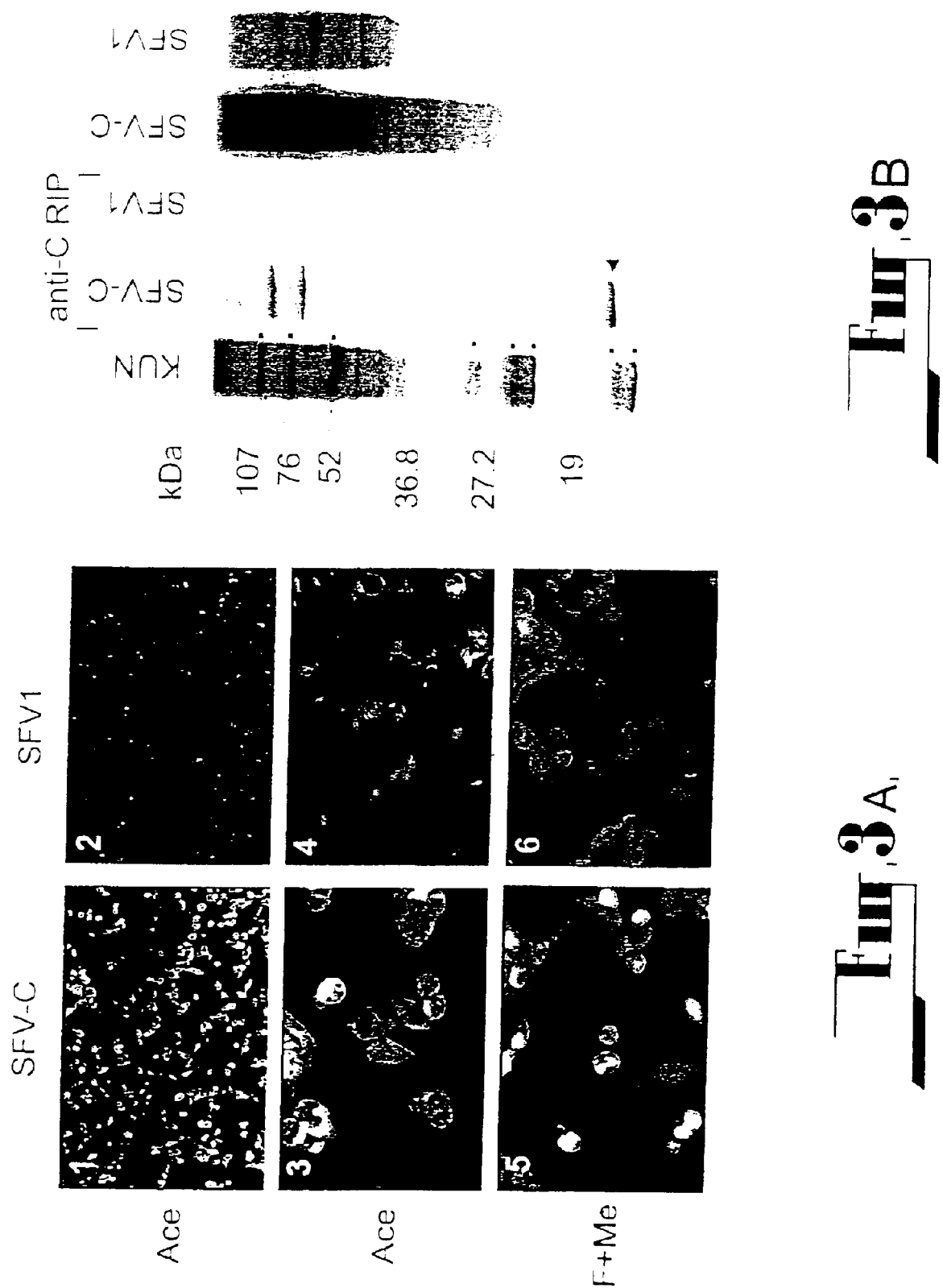
FIG. 3 illustrates expression of KUN C protein by recombinant SFV-C replicon. A) Immunofluorescence analysis of BHK21 cells at 18 h after transfection with SFV-C RNA (SFV-C, panels 1, 3, and 5) using KUN anti-C antibodies. SFV1 (panels 2, 4, and 6) represents IF of cells transfected with the control SFV1 RNA prepared from pSFV1 vector. Cells in panels 1 and 2 were photographed at lower magnification then in panels 3 to 6. Ace is an abbreviation for acetone fixation, F+Me is an abbreviation for formaldehyde-methanol fixation. B) Metabolic labelling with $^{35}$S-methionine/cysteine and radioimmunoprecipitation analysis with antibodies to C protein (+anti-C) of SFV-C and SFV1 transfected BHK21 cells. BHK21 cells in 60 mm culture dishes at 18 h after transfection were continuously labelled with 50 µCi/ml of $^{35}$S-methionine/cysteine for 4 h. Labelled cell lysates and radioimmunoprecipitates were prepared and samples were electrophoresed in a 15% polyacrylamide gel. Sample volumes were 1 µl of 500 µl in SFV-C, 0.5 µl of 300 µl in SFV1, 10 µl of 30 µl radioimmunoprecipitate from 160 µl of both SFV-C and SFV1 (+anti-C) cell lysates. Dots indicate the location of KUN proteins NS5, NS3, E, NS4B, prM, NS2A, C, and NS4A/NS2B (from top to bottom) in the radiolabeled KUN infected cell lysate. The arrow shows position of KUN C protein. Numbers represent molecular weights of low range pre-stained Bio-Rad protein standards. This and following figures were prepared by scanning all the original data (slides, autoradiograms, etc.) on the Arcus II scanner (Agfa) using FotoLook software (Agfa) for Macintosh at 150 lpi resolution, followed by assembling of the montages using Microsoft PowerPoint 97 software and printing on Epson Stylus Color 800 printer at 720–1440 dpi resolution using Epson photo quality ink jet paper.

Electroporation of SFV-C RNA into BHK21 cells resulted in expression of KUN C protein in almost 100% of cells as judged by IF with antibodies to KUN C protein (FIG. 3A, panel 1). KUN C protein expressed in SFV-C RNA transfected cells was localised in the cytoplasm (FIG. 3A, panel 3; acetone fixation) and also in the nuclei (FIG. 3A, panel 5; formaldehyde-methanol fixation). Because of difficulties in identification of KUN C protein in radiolabeled lysates of SFV-C transfected cells (FIG. 3B), immunoprecipitation of the radiolabelled lysates with anti-C antibodies was carried out. A labelled band coincident in migration with KUN C protein was apparent in the lysates of SFV-C but not in those of SFV1 transfected cells (compare SFV-C and SFV1 in FIG. 3B).

Expression of KUN prME Genes by the Recombinant SFV-prME Replicon.

The full-length prME sequence plus the preceding signal sequence in our SFV-prME construct (see FIG. 2) was included in the replicon. As a source of cDNA for prME genes, full-length KUN cDNA clone FLBSDX were used. An initiation and a termination codon, as well as BglII sites for conventional cloning, were incorporated into the primers for PCR amplification (see FIG. 2). To minimise the amount of possible mismatches which could occur during PCR amplification high fidelity Pfu DNA polymerase (Stratagene) was used in all our PCR reactions.

Figure 4:
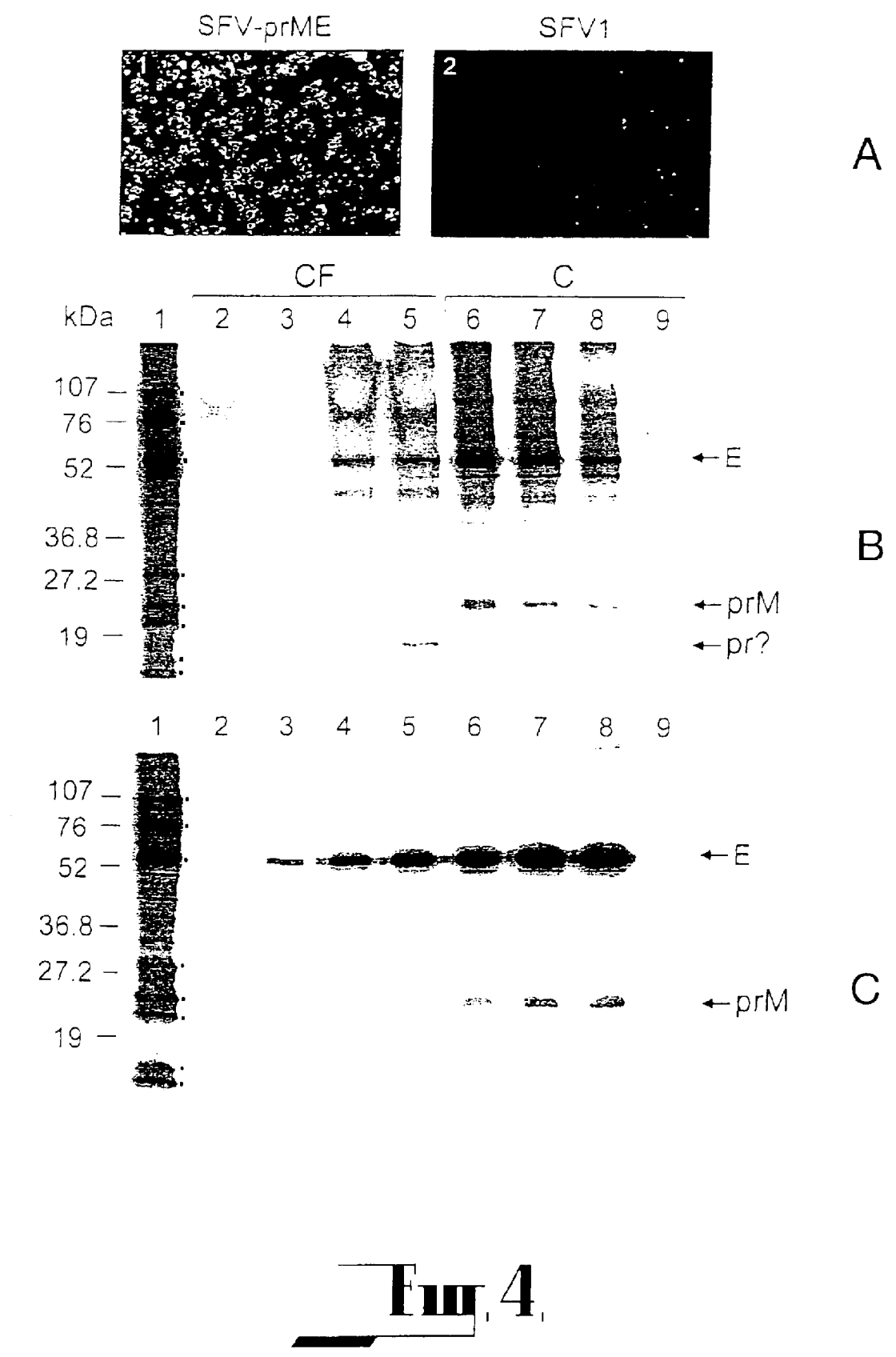

When SFV-prME RNA was electroporated into BHK21 cells, nearly 100% of cells were found to be positive in IF analysis with monoclonal antibodies to KUN E protein at 12–18 h after electroporation (FIG. 4A, panel 1). To confirm expression of KUN prM and E proteins in transfected cells and to detect secretion of prME into the tissue culture fluid transfected cells were labelled with $^{35}$S-methionine/cysteine for 1 h, followed by incubation for increasing chase periods.

A strongly labelled band corresponding to KUN E protein was apparent in both culture fluid and cell lysates of SFV-prME transfected cells at all times (see culture fluid and cells in FIG. 4B). A labelled band corresponding to KUN prM protein was detected only in cell lysates (cells in FIG. 4B). A labelled band corresponding in migration to the predicted molecular weight of KUN pr protein was detected in the culture fluid only of transfected cells (culture fluid in FIG. 4B).

An apparent increase in the intensity of labelling of E and possibly pr proteins in the culture fluid (FIG. 4B, culture fluid) and a concomitant decrease in the intensity of labelling of E and prM proteins in the cell lysates (FIG. 4B, cells) were observed during the chase period. The efficiency of the secretion of E and pr proteins was low, since the lanes showing labelled culture fluid were exposed to X-ray film for about 5 times longer than the lanes showing cell lysates (see legend to FIG. 4).

When samples from the pulse-chase labelling experiment with SFV-prME replicon were immunoprecipitated with KUN anti-E monoclonal antibodies, E and prM were coprecipitated from the transfected cell lysates (FIG. 4C, lanes 6–9), E protein (FIG. 4C, lanes 3–5) and in some experiments trace amounts of prM protein (results not shown) were precipitated also from culture fluid of transfected cells. Because of its low molecular weight, M protein probably ran off the gel during electrophoresis and therefore could not be detected. A gradual increase in the amount of immunoprecipitated labelled E protein in the culture fluid of transfected cells was observed throughout the chase period (FIG. 4C, lanes 3–5), confirming the ongoing secretion of E protein. An absence of correlation between the increase of immunoprecipitated labelled E protein in the culture fluid, and an expected decrease of labelled E and prM proteins immunoprecipitated from the cell lysate (compare lanes 3–5 in FIG. 4C with the corresponding culture fluid lanes in FIG. 4B, and lanes 6–9 in FIG. 4C with the corresponding cell lanes in FIG. 4B), can probably be explained by inadequate amounts of antibodies used for immunoprecipitation of a large excess of expressed proteins retained in the cells during the relatively short chase periods. Taken together, results of the direct pulse-chase labelling and RIP analyses confirmed both the correct processing of prME polyprotein in cells and the secretion of E, and possibly pr and M proteins, into the culture fluid after transfection of SFV-prME RNA into BHK21 cells.

Expression of all Three KUN Structural Proteins by the Recombinant SFV-prME-C Replicon.

Although KUN replicon was packaged using transfection with two SFV RNAs expressing prME and C genes separately (see results in the next example), the efficiency of packaging was low. To increase the efficiency of packaging and to simplify the procedure a single SFV replicon construct was prepared expressing prME genes and C gene simultaneously. Because of the difficulties experienced with cloning of the entire C-prM-E region into the pSFV1 vector (see the first section of the Results) and also in order to avoid possible uncertainty regarding cleavage at the carboxy terminus of C in the absence of flavivirus protease NS2B-NS3, an SFV replicon expressing prME and C genes under the control of two separate 26S promoters was prepared (see SFV-prME-C in FIG. 2).

IF analysis of SFV-prME-C electroporated BHK cells with anti-E and anti-C antibodies showed expression of both E and C proteins in nearly 100% of cells by 18 h after transfection (results not shown). Both E and C proteins were expressed in the same cell (compare dual labelling by anti-C and anti-E antibodies in FIG. 5A). When transfected cells were pulse-chased with $^{35}S$-methionine/cysteine and the lysates were immunoprecipitated with KUN anti-E monoclonal antibodies, both E and prM proteins were coprecipitated, as was observed after transfection of SFV-prME RNA (compare FIG. 4B and FIG. 5B). A gradual increase of immunoprecipitated labelled E protein in culture fluids, and a corresponding decrease of immunoprecipitated labelled E and prM proteins in the cell lysates were observed during the chase period (FIG. 5B). Immunoprecipitation of the labelled cell lysates with anti-C antibodies confirmed expression of C protein in transfected cells and showed a gradual decrease of the amount of precipitated C during the chase period (FIG. 5C). The results of RIP analysis of culture fluid, not treated with detergents, using anti-C antibodies were negative (results not shown), indicating that no free C protein was secreted into culture fluid of SFV-prME-C transfected cells. In a later experiment (see FIG. 8C, lane 2), particles secreted from cells transfected only with SFV-prME-C RNA were purified and precipitated with anti-E antibodies; again no secreted C was detected.

Overall, the immunofluorescence and labelling patterns in cells transfected with SFV-prME-C RNA were very similar to those observed in cells transfected with two different RNAs expressing prME and C proteins separately (compare FIG. 5 with FIG. 3 and FIG. 4), suggesting proper processing and maturation of all three KUN structural proteins when expressed from the recombinant SFV replicon.

EXAMPLE 2

Preparation of Encapsidated Particles and Determination of their Titer

For all infections with encapsidated particles, cell culture fluid was filtered through a 0.45 μm filter (Sartorius AG, Gottingen, Germany) and treated with RNase A (20 μg per ml) for 0.5 h at room temperature (followed by 1.5 h incubation at 37° C. during infection of cells). To prepare partially purified particles, filtered and RNase A treated culture fluids from transfected cells were clarified by centrifugation at 16,000 g in the microcentrifuge for 15 min at 4° C., and the particles were pelleted from the resulting supernatant fluid by ultracentrifugation at 40,000 rpm for 2 h at 4° C. in the AH650 rotor of the Sorvall OTD55B centrifuge. The pellets were resuspended in 50 μl PBS supplemented with RNAse A (20 μg per ml), left to dissolve overnight at 4° C., and then used for infection of BHK21 cells or for RT-PCR analysis. To determine the titer of encapsidated particles, BHK21 cells on 1.3 $cm^2$ coverslips were infected with 100–200 μl of serial 10-fold dilutions of cell culture fluid or of pelleted material for 1.5 h at 37° C. The fluid was then replaced with 1 ml of DMEM medium supplemented with 2% FBS; cells were incubated for 24 h at 37° C. in the $CO_2$ incubator and then subjected to IF analysis with anti-NS3 antibodies as described above. The infectious titer of packaged particles was calculated using the following formula:

$$\text{Titer } (IU) \text{ per } 2\times10^5 \text{ of initially transfected cells} = N\times(SW{:}SIA)\times10^n\times(V{:}VI),$$

where N is the average number of anti-NS3 positive cells in the image area, calculated from 5 image areas in different parts of the coverslip; SW is the surface of the well in a 24-well plate (200 $mm^2$); SIA is the surface of the image area (1.25 $mm^2$ using defined magnification parameters, calculated according to the manual for the Wild MPS46/52 photoautomat [Wild Leitz, Heerburg, Germany]); V is the total volume of the culture fluid (usually 3–5 ml per 60 mm dish) collected from the population of $2\times10^6$ initially electroporated BHK21 cells; VI is the volume used for infection of the cover slips (usually 100–200 $\mu$l); and $10^n$ is the dilution factor.

Packaging of the KUN Replicon RNA into Transmissible "Infectious" Particles by the KUN Structural Proteins Expressed from the Recombinant SFV Replicons.

Because the KUN replicon construct C20rep was able to successfully transfect only 10–20% of cells a KUN replicon of greater transfection efficiency was used for attempted packaging in doubly transfected cells (i.e. KUN replicon, and recombinant SFV replicons expressing KUN structural proteins). This significantly improved the efficiency of transfection in BHK21 cells to about 80% using the replicon construct C20DXrep, which was used in all packaging experiments. As noted above, all cell culture fluids from packaging experiments were filtered to remove large membrane fragments and treated with RNase A to remove naked RNA.

Figure 8:
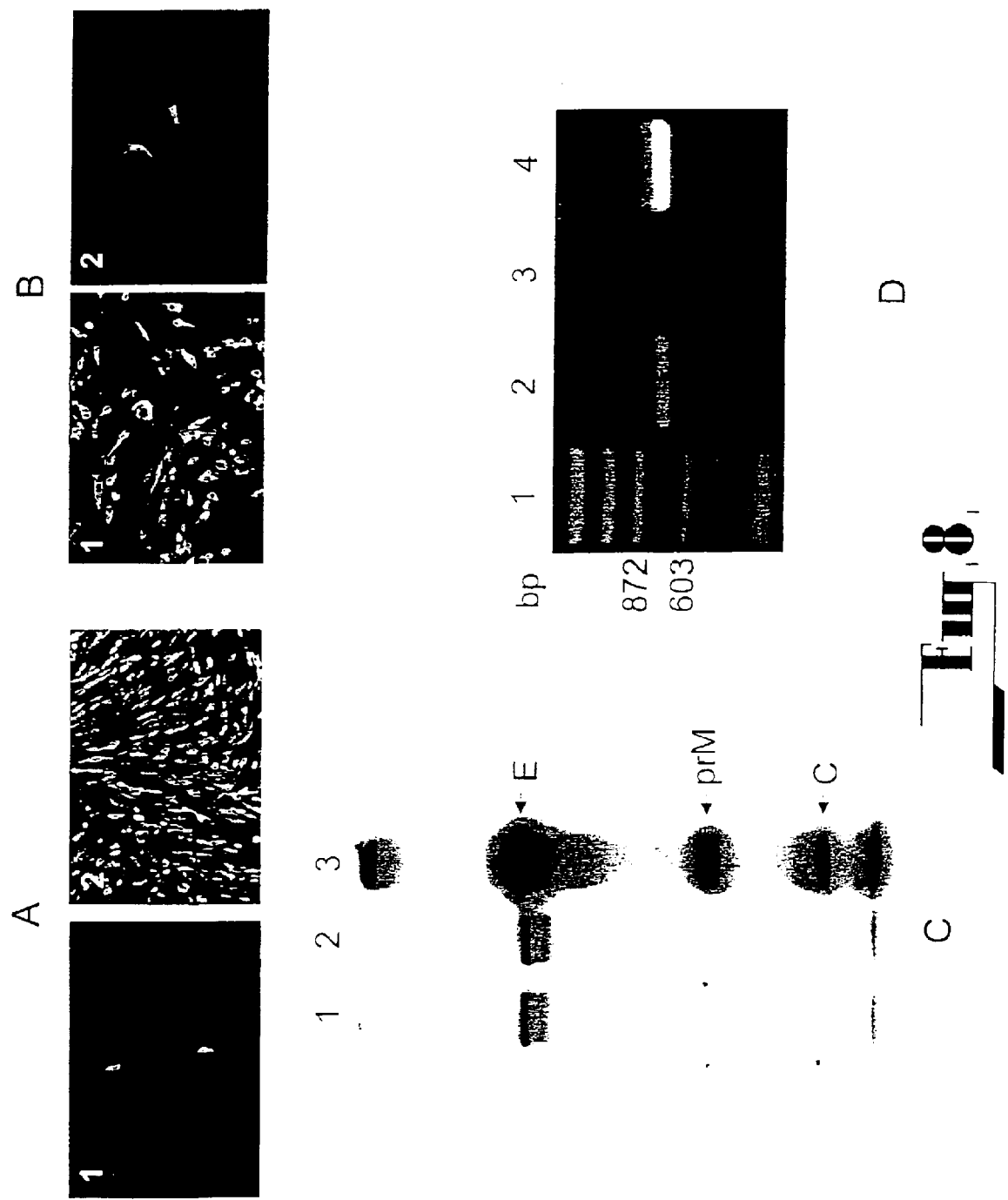
FIG. 8 illustrates characterisation of infectious particles. (A) Inhibition of infection with encapsidated particles, released from cells transfected sequentially with C20DXrep and SFV-prME-C RNAs (as in FIG. 6), by incubation with KUN anti-E monoclonal antibodies. Panel 1 represents IF with anti-NS3 antibodies of cells infected with culture fluid collected after the transfections and incubated with anti-E monoclonal antibodies for 1 h at 37° C. Panel 2 represents IF with anti-NS3 antibodies of cells infected with the same sample of culture fluid incubated under similar conditions in the absence of anti-E antibodies. (B) shows IF analysis with anti-N3 antibodies of cells infected with equal proportions of resuspended pellet (panel 1; 2 μl from 50 μl of total volume) or supernatant fluid (panel 2; 200 μl from 5 ml of total volume) from the culture fluid collected from cells transfected with C20DXrep and SFV-prME-C RNAs and subjected to ultracentrifugation. (C) Radioimmunoprecipitation analysis with anti-E antibodies of culture fluids from cells transfected with SFV-prME-C RNA (lane 2), sequentially transfected with C20DXrep and SFV-prME-C RNAs (lane 1), and infected with KUN virus (lane 3). Dots show faint bands corresponding to C and prM visible (in the original autoradiogram) in lane 1, but only a faint band for prM in lane 2. (D) RT-PCR analysis with KUN-specific primers of RNAs extracted from the anti-E-immunoprecipitates of culture fluid samples collected after transfection sequentially with C20DXrep and SFV-prME-C RNAs (lane 2), or after transfection only with SFV-prME-C RNA (lane 3), or after infection with KUN virus (lane 4). Lane 1 represents PhiX174 RF DNA digested with HaeIII (New England Biolab).

Initial cotransfection experiments showed that simultaneous transfection of C20DXrep RNA and SFV RNAs expressing KUN structural proteins did not result in the detection of infectious particles. Therefore a delay period of 12 h or longer between electroporations was used in subsequent experiments to allow KUN replicon RNA to accumulate before electroporation of SFV RNAs. IF and Northern blot analyses of BHK cells infected with the tissue culture fluid collected at 27 h after the first electroporation with C20DXrep RNA, and at 26 h after the second electroporation with recombinant SFV RNAs, showed higher efficiency of packaging when the single SFV-prME-C RNA was used compared to that obtained with two SFV RNAs, SFV-prME and SFV-C (compare panels 1 and 2 in FIG. 6A, and lanes 1 and 2 in FIG. 6B, respectively). Significantly, IF and Northern blot analysis showed that no released infectious particles containing replication competent SFV RNA were produced when SFV-prME-C RNA alone, or SFV-prME and SFV-C RNAs together, were transfected with (FIG. 6C, lanes 2 and 3) or without previous transfection of KUN replicon RNA. These results clearly demonstrated that the recombinant SFV replicon RNAs containing inserted KUN structural genes could not be packaged by the KUN structural proteins, hence the packaging was specific for KUN RNA. Also, no infectious particles containing packaged KUN replicon RNA were detected when only SFV-prME RNA was used in packaging experiments with C20DXrep RNA (panel 3 in FIG. 6A), demonstrating that coexpression of C protein is absolutely essential for the formation of the secreted infectious particles.

To optimize the conditions for efficient packaging of C20DXrep RNA in cotransfection experiments with SFV-prME-C RNA, variable time points between electroporations (FIG. 7A), and between the second electroporation and harvesting of the infectious particles (FIG. 7B), were examined. Initially optimisation of the time between the two electroporations was studied with a fixed time for collection of the infectious particles. Equal amounts of cells were seeded onto cell culture dishes after the first electroporation with C20DXrep RNA, and cells were subsequently electroporated with SFV-prME-C RNA at 12 h, 18 h, 24 h, or 30 h incubation intervals. Culture fluid was then harvested from each dish at 24 h after the second electroporation and serial dilutions were used to infect BHK21 cells. IF analysis of these cells with anti-NS3 antibodies indicated a gradual accumulation of infectious particles from 12 h to 24 h between electroporations, the highest titer reaching $3.8\times10^6$ infectious particles at 24 h from $2\times10^6$ of initially transfected cells (FIG. 7A). Northern blot analysis of total RNA from infected cells with a labelled KUN-specific cDNA probe showed that the optimal time interval between the electroporation of KUN replicon RNA and of SFV-prME-C RNA was between 18 h and 30 h (FIG. 7A). When the interval between electroporations was extended to 36 h and 48 h the yield of produced infectious particles was reduced.

In a separate study BHK cells were electroporated with SFV-prME-C RNA at 30 h after electroporation with C20DXrep RNA and seeded into one 60 mm culture dish. Single aliquot's of the culture fluid (1 ml of total 3 ml) were then collected at 24 h, 30 h, and 42 h after the second electroporation. The volume of the remaining culture fluid after removal of each aliquot was adjusted to the original volume by adding fresh media, and cells were re-incubated. Collected aliquots were then used to infect BHK cells and total cell RNA recovered from these infected cells at 24 h was then analysed for relative amounts of amplified KUN replicon RNA using IF analysis with anti-NS3 antibodies and Northern blot hybridization with a labelled KUN-specific cDNA probe. The gradual increase in amplified KUN replicon RNA from 24 h to 42 h after the second electroporation with SFV-prME-C RNA detected by Northern blot analysis (FIG. 7B) was in accord with an increase in released infectious particles as shown by IF analysis of newly infected cells with anti-NS3 antibodies.

In a separate experiments we compared efficiency of packaging using SFV replicon RNA SFV-prME-C105 expressing prME genes and a C gene coding precisely for the first 105 amino acids of KUN core protein (representing an exact copy of mature KUN core protein found in infectious virions) with that of SFV-prME-C RNA expressing prME genes and a C gene coding for the first 107 amino acids of KUN core protein plus an extra 4 amino acids derived from the vector (see FIG. 2). The same yields of encapsidated KUN replicon particles were obtained using either of these two RNAs (data not shown) indicating that extra 6 amino acids present in the core protein expressed from SFV-prME-C RNA (see FIG. 2) did not interfere with its packaging efficiency. Therefore both RNAs can be used for efficient production of encapsidated particles.

Characterisation of the Infectious Particles.

To prove that infectious particles secreted into the culture fluid of cells transfected with C20DXrep and SFV-prME-C105 RNAs were in fact virus-like particles incorporating KUN structural proteins, a virus neutralisation test was performed. An hour incubation of this tissue culture fluid at 37° C. with a 1/10 dilution of the cocktail of monoclonal antibodies to KUN E protein with known neutralising activity resulted in almost complete loss of infectivity (panel 1 in FIG. 8A), while no loss of infectivity was observed in the control sample incubated under similar conditions in the absence of antibodies (panel 2 in FIG. 8A). Similar results were obtained when incubations with antibodies were performed at room temperature or at 4° C.

To show that the infectious particles can be concentrated by pelleting, a clarified culture fluid of cotransfected cells was subjected to ultracentrifugation. When pellet and supernatant after ultracentrifugation were used to infect BHK cells which were later (at 24 h) analysed by IF with anti-NS3 antibodies, virtually all the infectious particles were present in the pelleted material (compare panels 1 and 2 in FIG. 8B).

To identify the proteins and to detect the presence of KUN replicon RNA in the recombinant infectious particles, they were immunoprecipitated in the absence of detergents from the culture fluid of cotransfected and radiolabeled cells using anti-E antibodies. Half of the immunoprecipitated sample was used for separation in the SDS-polyacrylamide gel, and the other half was used to extract RNA by proteinase K digestion. Radioautography of the polyacrylamide gel showed the presence of E, prM, and C proteins in the immunoprecipitates of culture fluid collected from cells either sequentially transfected with C20DXrep and SFV-prME-C RNAs or infected with KUN virus (FIG. 8C, lanes 1 and 3, respectively). E and prM proteins, but no C protein was immunoprecipitated from culture fluid of cells transfected only with SFV-prME-C RNA (FIG. 8C, lane 2), suggesting that specific interaction between KUN replicon RNA and KUN C protein was required for assembly of secreted infectious particles. Note that secreted flaviviruses often contain significant amounts of uncleaved prM as observed in FIG. 8C.

RNA extracted from the immunoprecipitates was reverse transcribed and PCR amplified using KUN-specific primers. A DNA fragment of predicted size (~700 bp, NS2A region) was observed in the RT-PCR reactions of RNAs extracted from the immunoprecipitates of the culture fluid collected from cells either transfected sequentially as in FIG. 6 with both C20DXrep and SFV-prME-C RNAs (FIG. 8D, lane 2) or infected with KUN virus (FIG. 8D, lane 4). No RT-PCR product was obtained from RNA extracted from the immunoprecipitate of the culture fluid collected from cells transfected with SFV-prME-C RNA alone (FIG. 8D, lane 3).

These analyses established that the infectious RNA recovered from packaging experiments was demonstrably packaged in particles encapsidated by the KUN structural proteins.

Further characterization of the packaged particles containing replicon RNA was performed by sedimentation analysis. In parallel with KUN virions (both concentrated by ultracentrifugation) they were sedimented through 5–25% sucrose density gradients. 0.5 ml fractions were collected, diluted and assayed for infectivity by IF assay using anti-NS3 antibodies at 18 h for KUN virions or at 24 h for replicon particles (see legend to FIG. 9A). The maximum infectivity for replicon particles was concentrated in fractions 5–7 with a peak titer of $\sim 1.3 \times 10^5$ IU/ml (fraction 6), while infectious KUN virions were mostly concentrated in fractions 2–4 with a peak titer of $\sim 2.8 \times 10^7$ IU/ml (fraction 3; FIG. 9A). These three fractions from each gradient were combined, incubated with anti-E antibodies to aggregate virions and encapsidated particles, and concentrated by ultracentrifugation for electron microscopy (for experimental details see legend to FIG. 9B). As might be expected from the gradient sedimentation results (FIG. 9A), particles containing encapsidated replicon RNA were smaller than KUN virions, ~35 nm diameter compared to ~50 nm diameter of virion particles (FIG. 9B). Both replicon and virion particles appeared to be spherical and uniform in size; surface details were not resolved, probably because of attachment of some anti-E antibody molecules (FIG. 9B).

EXAMPLE 3

Construction of Modified KUN Replicon Vectors and Expression of Heterologous Genes Cells.

BHK21 cells were grown in Dulbecco's modification of minimal essential medium DMEM, Gibco BRL) supplemented with 10% of fetal bovine serum (FBS). Vero cells were grown in M199 medium (Gibco BRL) supplemented with 5% FBS.

Construction of the Plasmids.

(I) C20DXrepNeo: The dicistronic replicon construct C20DXrepNeo used for generation of replicon-expressing BHK cells (repBHK) was prepared from C20DXrep by cloning an Ires-Neo cassette into the 3'UTR 25 nucleotides downstream of the polyprotein termination codon. An XmaI-XhoI fragment from ΔME/76Neo plasmid (Khromykh and Westaway, J. Virol. 1997, 71:1497–1505) representing nucleotides 10260–10422 of KUN sequence, followed by the IRES-Neo cassette and the last 522 nucleotides of KUN sequence was used to substitute XmaI$^{10260}$-XhoI$^{11021}$ fragment in C20DXrep construct. Note, that IRES-Neo cassette was initially derived from the mammalian expression vector plresNeo1 (a derivative of pCIN1, provided by S. Rees (Rees et al., BioTechniques, 1996, 20:102–110)). The nucleotide sequence at the C-terminus of IRES element in this IRES-Neo cassette was modified by authors in order to decrease the level of Neo expression thus forcing selection of cells expressing only high levels of inserted genes when using this (plresNeo1) vector and high concentrations of antibiotic G418.

Figure 10:
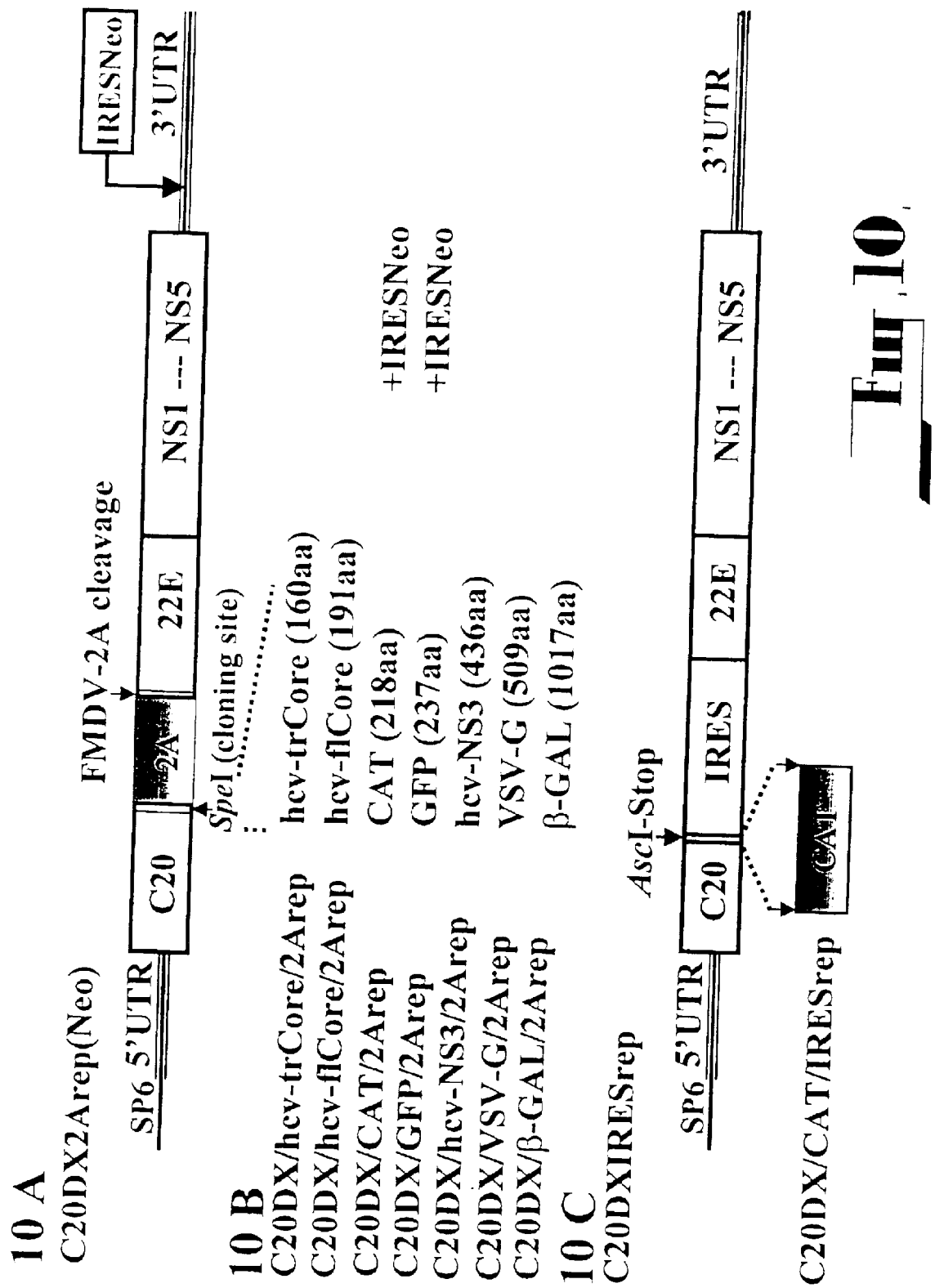
FIG. 10. Schematic representation of the Kunjin replicon expression vectors and recombinant constructs. (A) shows C20DX2Arep(Neo) vector(s) and its derivatives. SP6 shows the position of the SP6 promoter. 5'UTR and 3'UTR represent 5' and 3' untranslated regions, respectively. C20 corresponds to the first twenty amino acids of KUN Core protein. 22E corresponds to the last twenty two amino acids of KUN E protein. NS1-NS5 correspond to the sequence coding for KUN nonstructural proteins. 2A indicates sequence coding for 2A autoprotease of foot-and-mouth disease virus (FMDV) with its cleavage site indicated. IRESNeo represents a sequence of an internal ribosomal entry site (IRES) of encephalomyocarditis virus (EMCV) RNA followed by a sequence coding for the neomycin transferase gene (Neo). This cassette was inserted at the indicated position in the 3'UTR to obtain C20DX2ArepNeo vector for stable selection of replicon expressing cells (similar to $\Delta$ME/76Neo, Khromykh and Westaway, J. Virol., 1997, 71:1497–1505). SpeI shows a unique restriction site for cloning of heterologous genes. (B) shows a list of KUN replicons with heterologous genes inserted into the SpeI site of C20DX2Arep vector, hcv-trCore and hcv-flCore—sequences coding for the first 160 and 191 amino acids of hepatitis C virus Core protein, respectively: CAT—chloramphenicol acetyltransferase: GFP—green fluorescent protein, hcv-NS3—sequence coding for amino acids 183 to 617 of hepatitis C virus NS3 protein; VSV-G—glycoprotein G of vesicular stomatitis virus; $\beta$-GAL—*Escherichia coli*$\beta$-galactosidase. +IRESNeo signs opposite to CAT and GFP indicate that these genes were also cloned into C20DX2ArepNeo vector. (C) Dicistronic C20DXIRESrep vector and its derivative construct C20DX/CAT/IRESrep. AscI-Stop shows the position of a unique site for cloning of heterologous genes followed by the translation termination codon (Stop). The other abbreviations are as in (A).

(i) C20DX2Arep and C20DX2ArepNeo. To ensure cytosolic cleavage of heterologous genes expressed from the KUN replicon vectors, the C20Dxrep, C20DXrepNeo constructs were modified by inserting sequence coding for 2A autoprotease of the food-and-mouth disease virus (FMDV-2A) between the first twenty amino acids of KUN C and the last twenty two amino acids of KUN E proteins in each plasmid preserving the KUN polyprotein open reading frame. (C20DX2Arep, FIG. 10A). FMDV-2A peptide represents a specific sequence of 19 amino acids which cleaves itself at the C-terminus between the glycine-proline dipeptide and has been used to mediate cleavage of artificial polyproteins. The KUN replicon cDNA constructs C20DX2Arep and C20DX2ArepNeo (FIG. 10A) were prepared by cloning FMDV-2A sequence PCR amplified from the plasmid pT3CAT2A/NAmodII (Percy et al, J. Virol., 1994, 68:44864492, obtained from Peter Palese) using forward primer with incorporated MluI-SpeI restriction sites and reverse primer with incorporated EagI-MluI restriction sites, into AscI site of the previously described C20DXrep and C20DXrepNeo plasmids, respectively (FIG. 10A). High-fidelity Pfu DNA polymerase (Stratagene) was used for all PCR reactions.

Two unique sites for cloning of foreign genes were also incorporated into these vectors: (1.) a SpeI site between the first 20 amino acids of C protein and the 2A sequence, and (2.) a EagI site between the 2A sequence and the rest of the KUN replicon sequence. Cloning into SpeI site ensures the correct cleavage of C20-FG-2A fusion protein from the rest of the KUN polyprotein sequence. Cloning into the EagI site permits correct N-terminus cleavage, but it will have its C-terminus fused to the 22aa of E protein.

(iii) C20DX/CAT/2Arep, and C20DX/CAT/2ArepNeo. The FMDV-2A-CAT sequence was PCR amplified from the plasmid pT3CAT2A/NAmodII (Percy et al., J. Virol. 1994, 68:44864492), by using the same as for FMDV-2A amplification reverse primer and a forward primer with incorporated MiuI restriction site, and cloned into the AscI site of the C20DXrep and C20DXrepNeo plasmids to obtain C20DX/CAT/2Arep, and C20DX/CAT/2ArepNeo constructs, respectively (FIG. 10B).

(iv) C20DXIRESrep and C20DX/CAT/IRESrep. C20DXIRESrep was constructed by cloning EMCV IRES sequence PCR amplified from ΔME/76Neo plasmid (Khromykh and Westaway, J. Virol., 1997, 71:1497–1505) using the appropriate primers with incorporated AscI (forward primer) and MluI (reverse primer) restriction sites into the AscI site of the C20DXrep plasmid. C20DX/CAT/IRESrep construct was prepared by cloning CAT gene PCR amplified from the plasmid pT3CAT2A/NAmodII (Percy et al., J. Virol. 1994, 68:4486–4492) using primers with incorporated MluI restriction sites into the AscI site of C20DXIRESrep plasmid (FIG. 10C).

(v) C20DX/GFP/2Arep, C20DX/GFP/2ArepNeo, C20DX/hcvCORE160/2Arep, C20DX/hcvCORE191/2Arep, C20DX/hcvNS3/2Arep, C20DX/VSV-G/2Arep, and C20DX/β-GAL/2Arep. All these constructs (FIG. 10B) were prepared in a similar way as follows. The heterologous genes were PCR amplified from corresponding plasmids using primers with incorporated SpeI and/or XbaI restriction sites (sequences of the primers may be obtained from the corresponding author), and cloned into the SpeI site of the C20DX2Arep or C20DX2ArepNeo (FIG. 10A). Plasmids for PCR amplifications of the above genes were: GFP—pEGFP (Clontech), hcv Core—pcDNA3/HCV-Core (obtained from Eric Gowans, Sir Albert Sakzewski Virus Research Center, Brisbane), hcvNS3—p3B-271 (obtained from Eric Gowans), VSV-G—pHCMV19 (obtained from Michael Bruns, Heinrich-Pette-Institute, University of Hamburg), β-GAL—pSFV3/LacZ (Gibco BRL).

RNA Transcription and Electroporation.

Recombinant KUN replicon RNA transcripts were prepared using SP6 RNA polymerase from the corresponding recombinant KUN replicon plasmid DNAs linearized with XhoI or from the SFV-prME-C105 plasmid linearized with SpeI. Electroporation of RNAs into BHK21 cells was performed according to the method described in Example 1.

Immunofluorescence Analysis.

Figure 11:
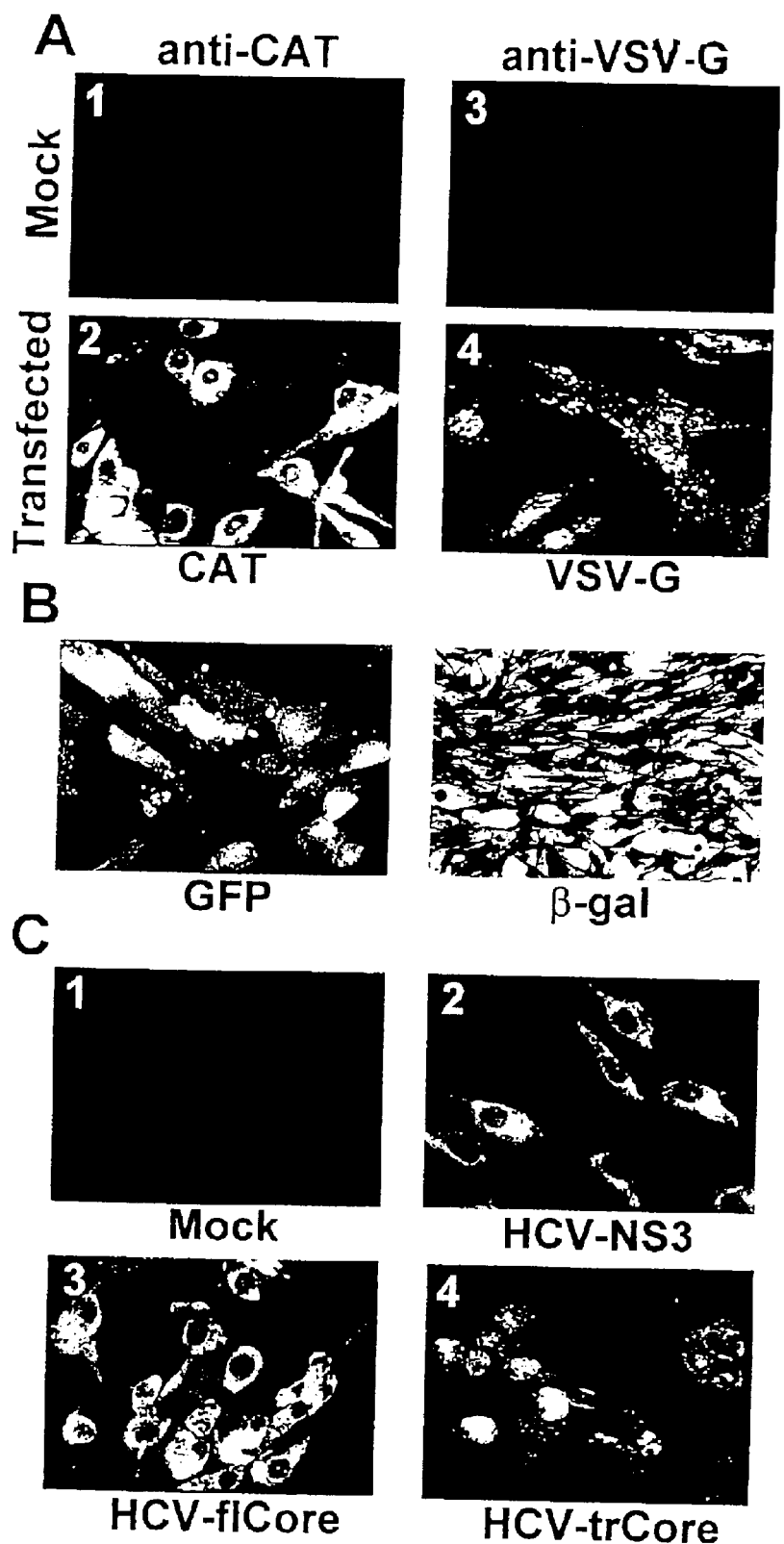
FIG. 11. Expression of heterologous genes in BHK21 cells electroporated with recombinant RNAs. (A) and (C) show IF analysis of BHK21 cells at 24 to 40 hours after transfection with the recombinant KUN replicon RNAs expressing different heterologous genes (indicated under each panel) using corresponding antibodies. Dilutions of antibodies were as follows: 1/100 for rabbit anti-CAT polyclonal antibodies (panels 1 and 2 in A); 1/150 for rabbit anti-VSV-G polyclonal antibodies (panels 3 and 4 in A); 1/40 for human anti-HCV polyclonal serum (panels 1–4 in C). Mock show parallel IF analyses of untransfected BHK21 cells. (B) GFP panel shows fluorescence of live unfixed BHK21 cells at 24 h after transfection with C20DX/GFP/2Arep RNA. $\beta$-Gal panel represents X-gal staining of BHK21 cells at 46 h after transfection with C20DX/$\beta$-GAL/2Arep RNA performed as described in the examples.
Figure 12:
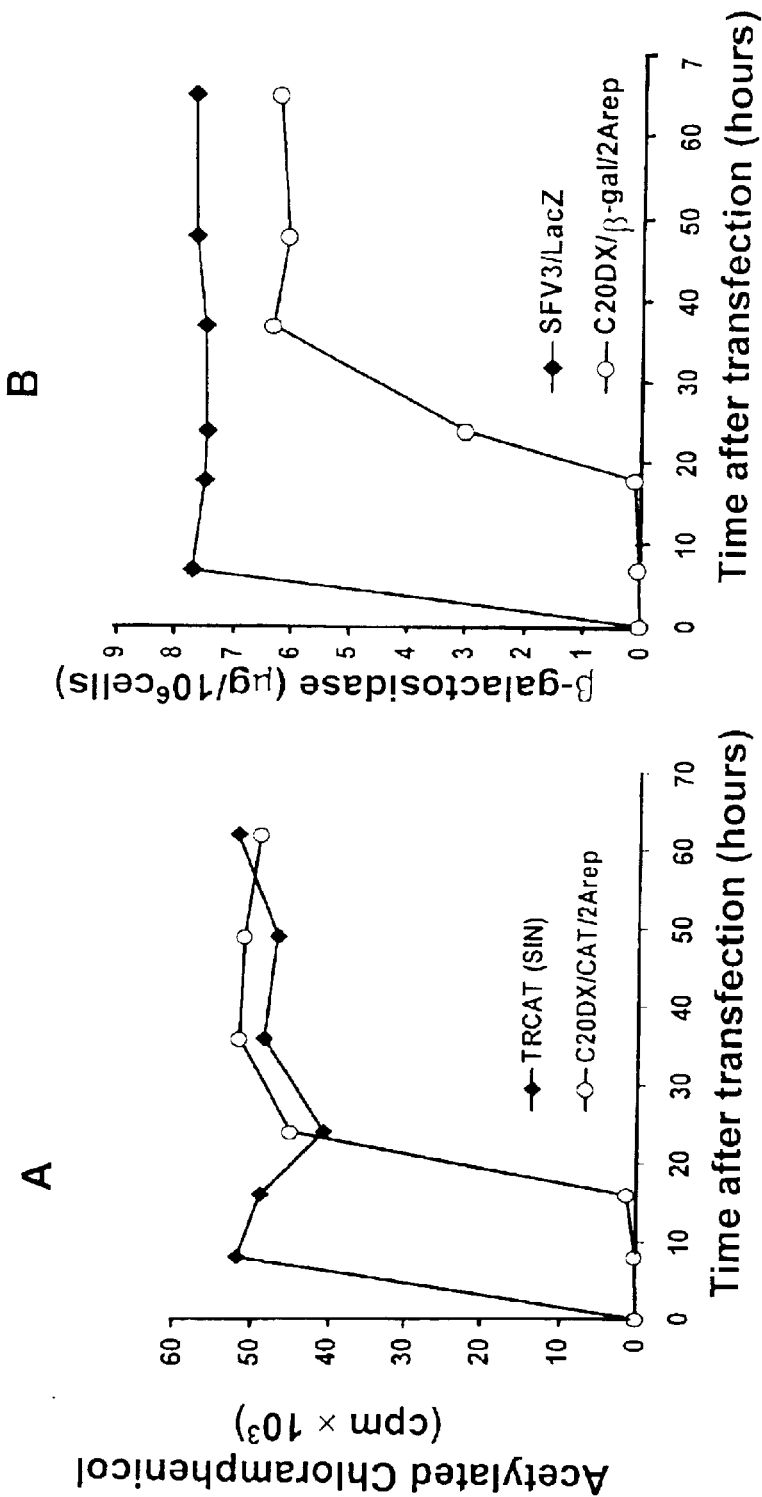
FIG. 12. Time course analyses of the CAT and $\beta$-GAL expression in cells transfected with corresponding recombinant KUN replicon RNAs. (A) Comparative analysis of CAT expression in BHK21 cells at different times after transfection with the same amounts (~10 $\mu$g) of KUN replicon (C20DX/CAT/2Arep) or Sindbis replicon (TRCAT) RNAs. CAT activity is expressed in cpm/min of radioactive acetylated chloramphenicol determined by LSC CAT assay as described in the examples. Because of a severe cytopathic effect, incubation of cells transfected with TRCAT RNA was aborted after 24 h post transfection. (B) Comparative analysis of $\beta$-galactosidase expression in BHK21 cells after transfection with the same amounts (~5 $\mu$g) of C20DX/$\beta$-GAL/2Arep or SFV3/LacZ RNAs. Expression of $\beta$-galactosidase ($\mu$g per $10^6$ cells) was calculated from the comparison of the results of $\beta$-galactosidase assay of the transfected cell lysates and $\beta$-galactosidase enzyme standard using $\beta$-GAL Enzyme Assay System Kit (Promega, Madison, Wis., USA) essentially as described by the manufacture (see the examples).

Immunofluorescence (IF) analysis of electroporated or infected cells was performed as described using antibodies specific to expressed proteins or KUN anti-NS3 antibodies. Rabbit polyclonal anti-CAT antibodies were purchased from 5 Prime →3 Prime (Boulder. Colo., USA), rabbit polyclonal anti-VSV-G antibodies were obtained from Michael Bruns (Heinrich-Pette-Institut, Hamburg, Germany), human anti-HCV polyclonal serum was provided by Eric Gowans (Sir Albert Sakzewski Virus Research Centre, Brisbane, Australia). Preparation and characterization of KUN anti-NS3 antibodies were described previously (Westaway et al., J. Virol., 1997, 71:6650–6661).

In Situ β-Galactosidase Staining and β-Galactosidase Assay.

X-gal staining of BHK21 cells either electroporated with C20DX/β-GAL/2Arep RNA or infected with VLP containing encapsidated C20DX/β-GAL/2Arep RNA and determination of β-galactosidase activity in the cell lysates was performed using commercial β-GAL Enzyme Assay System Kit (Promega, Madison, Wis., USA) essentially as described by the manufacture.

CAT Assay.

CAT activity in lysates of BHK21 cells either electroporated with TRCAT and C20DX/CAT/2Arep RNAs, or after infection with VLPs containing encapsidated C20DX/CAT/2Arep RNA, or in stable cell line expressing C20DX/CAT/2ArepNeo RNA was determined using TLS or LSC assays as described previously (Khromykh and Westaway, J. Virol., 1997, 71:1497–1505).

Preparation of Encapsidated Particles and Determination of their Titer.

Preparation of the recombinant VLPs expressing CAT, GFP, and VSV-G proteins and determination of their titers was performed as described in Example 1.

Optimal time of expression of heterologous products: In order to estimate the level and the optimal time of expression of heterologous products using this system, as well as to evaluate possible effects of the size of inserted sequences on the replication and packaging efficiency of resulting recombinant KUN replicon RNAs, KUN replicons expressing CAT (218 amino acids), GFP (237 amino acids), and β-Gal (1017 aa) genes were prepared in C20DX2Arep vector (FIG. 10B). In addition, CAT gene was also inserted into C20DXIRESrep vector producing C20DX/CAT/IRESrep RNA (FIG. 10C). To demonstrate proper glycosylation of expressed glycoproteins in our system a C20DX/VSV-G/2Arep construct expressing VSV G glycoprotein (FIG. 10B) was prepared. The expression of these genes in electroporated BHK21 cells was initially demonstrated by IF analysis with specific antibodies for CAT and VSV-G proteins (FIG. 11A), by fluorescence analysis of live unfixed cells for GFP protein (panel 1 in FIG. 11B), and by X-gal staining for β-Gal protein (panel 2 in FIG. 1B). The percentage of expressing cells in these experiments varied amongst the constructs from ~10% for C20DX/CAT/IRESrep RNA, ~20% for C20DX/β-Gal/2Arep, C20DX/VSV-G/2Arep, and C20DX/CAT/2Arep RNAs to ~50% for C20DX/GFP/2A RNA at 24–48 after electroporation (data not shown). In a separate experiment ~80–90% cells were transfected with C20DX/β-Gal/2Arep RNA.

Expression of HCV Proteins.

To express HCV proteins using the KUN replicon system, Core and NS3 genes of an Australian isolate of HCV (Trowbridge and Gowans, Arch. Virol., 1998, 143:501–511) were expressed using the replicon vector C20DX2Arep. A truncated form of HCV NS3 gene (coding for amino acids 183 to 617), containing most of the HCV NS3 cytotoxic T cell epitopes was cloned into C20DX2Arep vector. Transfection of the recombinant C20DX/hcvNS3/2Arep RNA into BHK21 cells resulted in detection of expression of HCV NS3 gene in ~20–30% of transfected cells (panel 2 in FIG. 11C). HCV Core gene was expressed in two forms: as a full length gene (coding for 191 amino acids, C20DX/hcv-flCore/2Arep RNA, FIG. 10B), and as a truncated gene (coding for the first 160 amino acids, C20DX/hcv-trCore/2Arep RNA, FIG. 10B). Electroporation of both RNAs into BHK21 cells resulted in expression of HCV Core protein in ~60–70% of transfected cells (data not shown), and at a similar levels, as judged by the intensity of IF with human anti-HCV antiserum (FIG. 11C, panels 3 and 4). Significantly, similar to the reports on expression of different forms of HCV Core in other systems, truncated HCV Core expressed from KUN replicon vector was localized in the nuclei, while full-length Core was not (data not shown).

Kinetics of Expression, Processing and Glycosylation of Heterologous Proteins Using KUN Replicon Vectors.

The kinetics of expression of two different size reporter genes CAT (218 amino acids) and β-Gal (1017 amino acids) after electroporation of corresponding recombinant replicon RNAs into BHK21 cells were compared by appropriate reporter gene assays. Similar to previous results with detection of replicating KUN replicon RNA, a delay of about 10–16 h in detectable expression of both reporter genes was observed (FIG. 12). Further incubation of electroporated cells resulted in a rapid accumulation of CAT protein, reaching maximum at ~30 h after transfection (FIG. 12A), while accumulation of β-Gal protein was slightly delayed, reaching maximum at ~36–40 h after transfection (FIG. 12B). In parellel experiments, expression of CAT gene from SIN replicon (TRCAT in FIG. 12A) and LEGAL gene from SFV replicon (SFV3/LacZ in FIG. 12B) reached maximum level earlier after transfection (6–8 h) and remained approximately at the same level during the experiment. The maximum levels of expression of the CAT and β-GAL genes in cells electroporated with the same amounts of alphavirus replicon RNAs and corresponding KUN replicon RNAs were similar (FIGS. 12A and B). Quantitative analysis of β-GAL expression showed that ~6–7 μg and ~7–8 μg of β-GAL protein per $10^6$ initially transfected cells was produced from ~5 μg of electroporated C20DX/β-GAL/2Arep and SFV3/LacZ RNAs, respectively (FIG. 12B). Importantly, in contrast to the massive destruction of cells expressing β-GAL from SFV replicon RNA (data not shown), cells expressing β-GAL from KUN replicon looked quite healthy (see for example FIG. 11B).

To examine whether proper proteolytic cleavage mediated by FMDV-2A protease occurred during translation of recombinant KUN replicon RNAs in electroporated cells, the sizes of the radiolabelled protein products expressed from C20DX/CAT/2Arep RNA were examined using radio-immunoprecipitation (RIP) analysis with anti-CAT antibodies. Strong radiolabelled band of ~30 kDa, corresponding to a predicted size of C20/CAT/2A fusion protein (257 amino acids) was observed (lane 1, FIG. 13A), suggesting that FMDV-2A cleavage indeed occurred. The presence of a very weak band of ~33 kDa, corresponding to the predicted size of C20/CAT/2A/22E fusion protein (286 amino acids) was also observed (lane 1, FIG. 13A), indicating that the cleavage by FMDV-2A protease was not complete. However, comparative analysis of the relative intensities of these two bands clearly demonstrated that most of the fusion protein (~95–98%) was efficiently cleaved. Note that the cleavage between 22E and NS1 (FIG. 10A) is mediated by cellular signal peptidase.

Figure 13A:
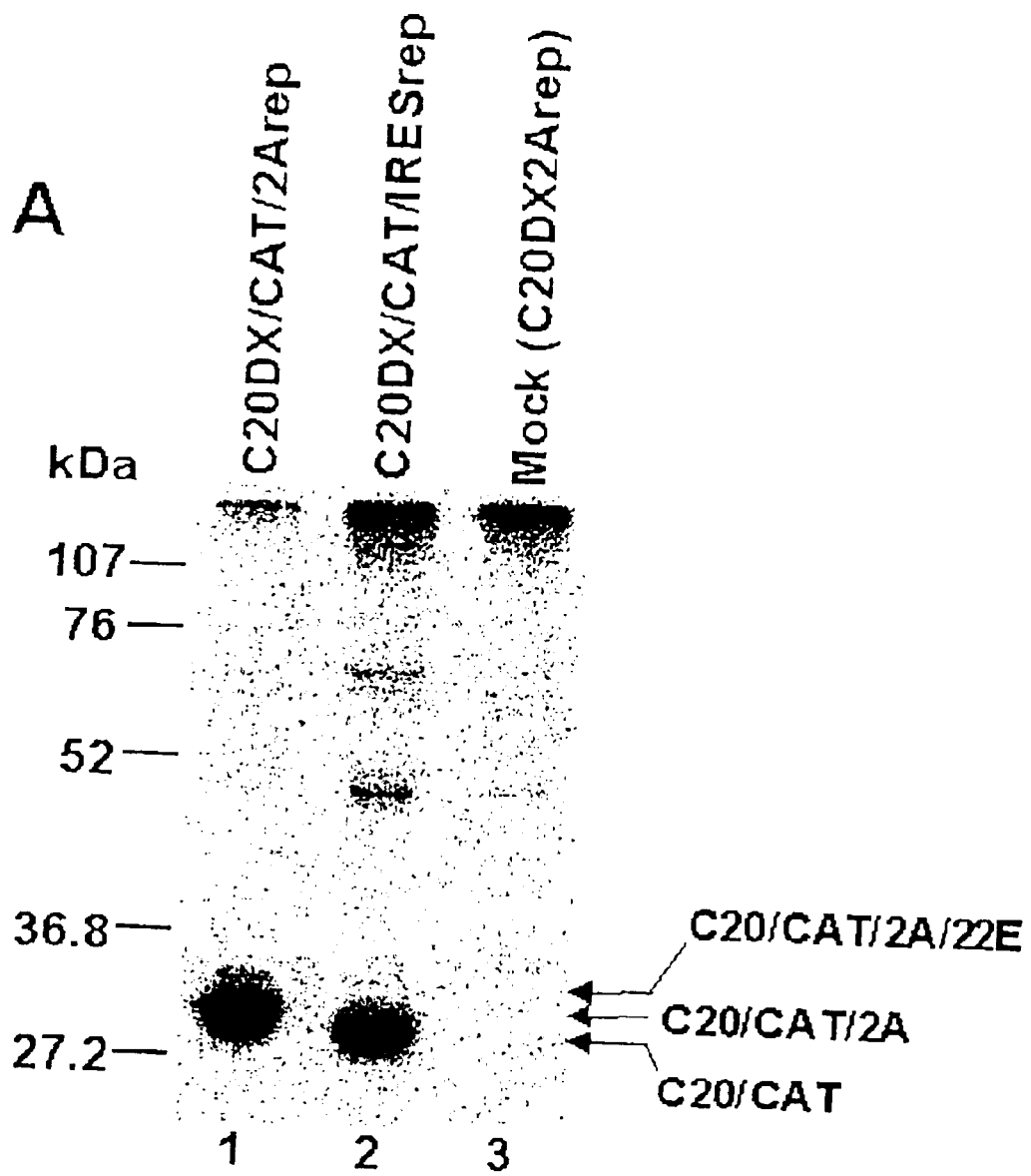
FIG. 13. Processing of polyproteins translated from the electroporated recombinant KUN replicon RNAs. (A) Radioimmunoprecipitation (RIP) analysis of radiolabelled BHK21 cells transfected with C20DX/CAT/2Arep (lane 1), C20DXCAT/IRESrep (lane 2), and C20DX2Arep (lane 3) RNAs using anti-CAT antibodies. 60 mm-diameter tissue culture dishes of BHK21 cells at 46 h after electroporation with corresponding RNAs were labeled with ~100 $\mu$Ci of [$^{35}$S]-methionine-cysteine for 5 h and RIP analysis of cell lysates was performed using 1/100 dilution of anti-CAT antibodies. Samples recovered after RIP analysis were electrophoresed on SDS-12.5% polyacrylamide gel. Arrows show the positions of corresponding CAT fusion protein products. (B) RIP analysis with rabbit anti-VSV-G antibodies (1/100 dilution) of BHK21 cells electroporated with C20DX/VSV-G/2Arep (lanes 1 and 2) and C20DX2Arep (lane 3) RNAs. 60 mm-diameter tissue culture dishes of BHK21 cells at 33 h after electropration were labeled with ~50 $\mu$Ci of [$^{35}$S]-methionine-cysteine for 8 h. One half (10 $\mu$l) of C20DX/VSV-G/2Arep RIP sample was treated with endoglycosidase F (endo F) as described elsewhere and both endo F-treated and untreated samples were electrophoresed on SDS-10% polyacrylamide gel. Arrows show the positions of glycosylated (gVSV-G) and nonglycosylated (VSV-G) proteins.
Figure 13B:
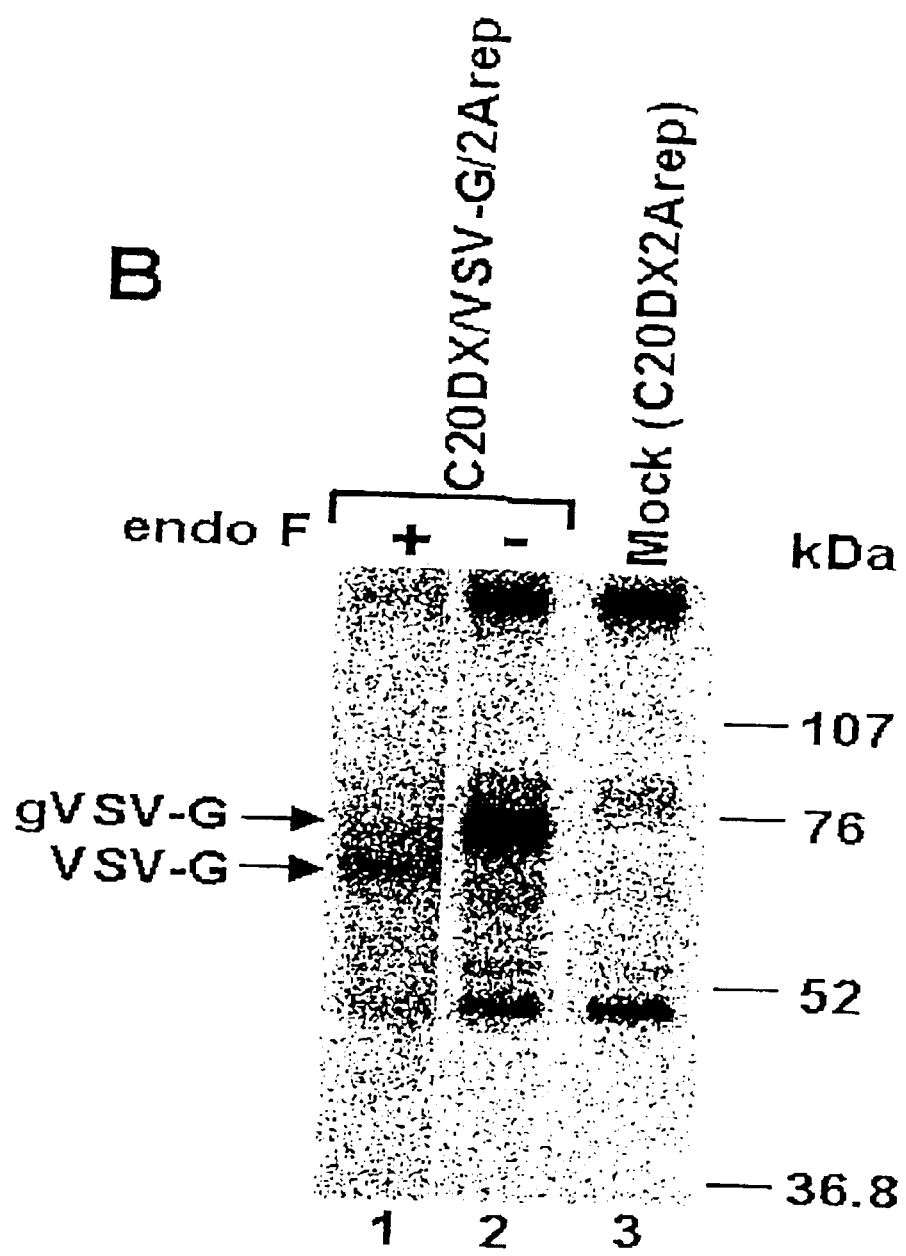

Expression and proper processing of heterologous genes from the dicistronic KUN replicon vector C20DXIRESrep was demonstrated by detection of ~27.5 kDa radiolabelled band corresponding to a predicted size of C20CAT protein (240 amino acids) in the anti-CAT immunoprecipitate from the lysate of BHK21 cells transfected with C20DX/CAT/IRESrep RNA (lane 2, FIG. 13A). Glycosylation of the VSV-G glycoprotein expressed from KUN replicon was demonstrated by the observed reduction in size of the endoglycosidase F treated VSV-G protein immunoprecipitated from the radiolabbeled lysates of BHK21 cells transfected with C20DX/VSV-G/2Arep RNA (compare lanes 1 and 2 in FIG. 13B).

Packaging of Recombinant KUN Replicon RNAs into Pseudoinfectious Virus-Like Particles.

Although relatively high level of expression of heterologous genes was achieved in BHK21 cells after electroporation of recombinant KUN replicon RNAs, it is well known that the efficiencies of transfection of different cell lines varies tremendously. Therefore it was desirable to prepare a stocks of virus-like particles (VLP) containing encapsidated recombinant replicon RNAs in order to broaden the spectrum of cells which could be used for expression. According to the present invention a heterologous packaging system has been developed allowing production of VLPs containing KUN replicon RNA encapsidated by the KUN structural proteins using consecutive transfections with KUN replicon RNA and SFV replicon RNA SFV-prME-C105 expressing KUN structural genes. The highest titer of VLPs was achieved when the second electroporation with SFV-prME-C105 RNA was performed at the time of the maximum replication of KUN replicon RNA (delay of ~24–27 h). Therefore in packaging experiments with recombinant KUN replicon RNAs, second electroporation with SFV-prME-C105 RNA was performed at the estimated time of maximum replication of recombinant KUN replicon RNAs (for time intervals see legend to FIG. 14).

Essentially all recombinant replicon RNAs were packaged into VLPs (FIG. 14), albeit with different efficiencies. The lowest efficiency of packaging was obtained for replicon RNAs expressing HCV Core protein (~$10^3$ infectious units (IU) per ml, results not shown), suggesting strong interference of HCV Core gene sequence or its protein product with the encapsidation of recombinant KUN replicon RNA. The titers of extracellular VLPs recovered in the packaging experiments with other recombinant RNAs were all in a range of $10^5$–$10^6$ IU per ml depending on the type of cells used for infectivity assays (Vero or BHK21) and the inserted sequence (results not shown). In general, higher titers were obtained when infectivity assays were performed on Vero cells than on BHK21 cells, and when packaging was performed with recombinant KUN replicon RNAs possessing higher initial transfection/replication efficiency. Similar amounts of infectious VLPs were also recovered from the lysates of transfected cells (results not shown).

Establishment of Stable Cell Lines Expressing CAT and GFP Genes Using C20DX2ArepNeo Vector.

Figure 15:
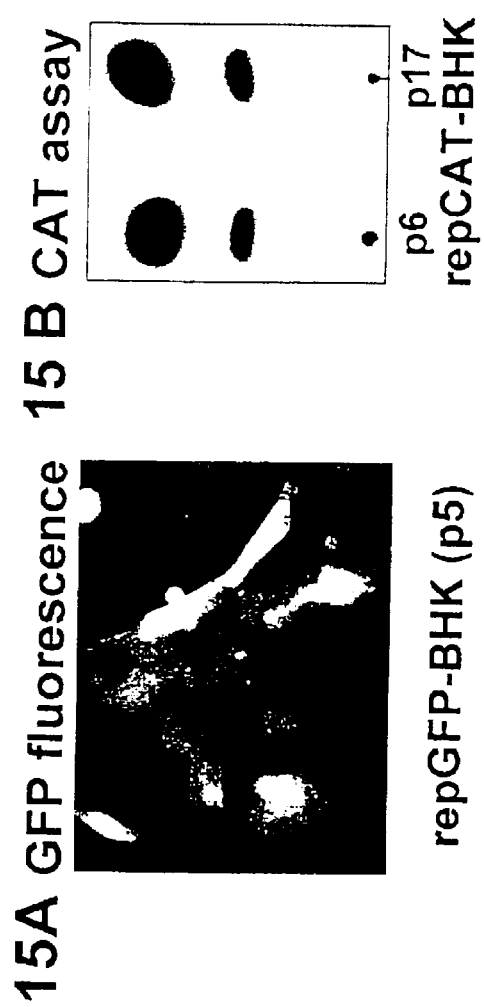
FIG. 15. Stable BHK cell lines expressing GFP (repGFP-BHK) and CAT (repCAT-BHK). Cell lines were established by selection of BHK21 cells transfected with C20DX/GFP/2Arep and C20DX/CAT/2Arep RNAs, respectively, in the medium containing 1 mg per ml of G418 (Geneticin). (A) GFP fluorescence of passage 5 of repGFP-BHK cells. (B) Autoradiogram of the CAT assay of the lysates from repCAT-BHK cells at passages 6 and 17.

To demonstrate the utility of this dicistronic KUN-Neo replicon vector for the establishment of stable cell lines expressing heterologous genes two constructs, C20DX/CAT/2ArepNeo and C20DX/GFP/2ArepNeo were prepared by cloning CAT and GFP sequences into the SpeI site of the C20DX2ArepNeo vector (FIGS. 10A and B). Transfection of the resulting RNAs into BHK21 cells and subsequent incubation of these cells in the medium supplemented with 1 mg/ml G418 (Geneticin) resulted in a rapid enrichment of cells expressing CAT and GFP genes (repCAT-BHK and repGFP-BHK, respectively; FIG. 15). Most of the cells in the total cell population were producing relatively high levels of heterologous protein (see for example FIG. 15A). Importantly, the level of expression remained stable during further passaging of the cells (compare CAT expression in repCAT-BHK cells at passages 6 and 17 in FIG. 15B).

The above examples show that noncytopathic flavivirus KUN replicon vectors can be used for transient or stable expression of heterologous genes in mammalian cells. They also show that recombinant KUN replicon RNAs expressing heterologous genes can be encapsidated into pseudoinfectious virus-like particles by subsequent transfection with SFV replicon RNA expressing KUN structural genes. These virus-like particles can be used for delivery of the recombinant self-replicating RNAs into a wide range of cells or animals leading to a long-term production of heterologous proteins. Importantly, because of the heterologous nature of the developed packaging system, no recombination between KUN and SFV RNAs producing an infectious virus can occur.

While the amounts of produced heterologous proteins using KUN replicon vectors were lower than those reported in using alphavirus replicon vectors, replication of KUN replicons in contrast to alphavirus replicons did not produce any cytopathic effect in cells. This noncytopathic nature and persistence of replication of KUN replicons allowed the development of a vector for generation of stable cell lines continuously expressing heterologous genes by inserting IRES-Neo cassette into the 3'UTR of C20DX2Arep replicon. Using such a selectable vector (C20DX2ArepNeo), a stable BHK cell lines continuously expressing GFP and CAT genes were rapidly established by selection of transfected cells with antibiotic G418. The expression of these genes in the established cells lines maintained at the same level for at least 17 passages.

EXAMPLE 4

Construction of Replicon Vector Containing Ubiquitin Gene

Mouse ubiquitin gene was PCR amplified from the plasmid pRB269 (Baker et al., J Biol Chem 269:25381–25386)

using appropriate primers with incorporated unique cloning sites (see FIG. 16A). Resulting PCR fragment containing also XbaI site at the 5'end and SpeI site at the 3'end was then cloned into the SpeI site of C20DX2Arep plasmid (see FIG. 10A), producing C20DXUb2Arep vector (FIG. 16). Thus the gene of interest can be cloned either between C20 and ubiquitin or between ubiquitin and FMDV 2A protease sequences (FIG. 16A). If heterologous sequence inserted between C20 and ubiquitin, the resulting product would be a fusion with C20 at the N-terminus and with ubiquitin at the C-terminus for efficient targeting to proteosomes. If heterologous sequence inserted between ubiquitin and FMDV2A, the resulting product would have a correctly processed N-terminus but would contain an FMDV 2A peptide fused to its C-terminus. Transfection of C20DXUb2Arep RNA into BHK21 cells resulted in its replication with efficiency similar to that of C20DXrep RNA (FIG. 16B).

EXAMPLE 5

Modified Kunjin Replicon Vector with HDV Antigenomic Ribozyme Sequence

To produce KUN replicon transcripts with authentic 3'-termini we incorporated hepatitis delta virus (HDV) antigenomic ribozyme sequence (Perrotta and Been, 1991, *Nature* (London) 350:434–436) followed by the simian virus 40 (SV40) polyadenylation signal (HDVribo/SV40polyA) immediately downstream of the last nucleotide of KUN replicon sequence (FIG. 17A). Delta virus ribozyme should cleave itself off either during in vitro transcription reaction or after transfection into cells thus releasing precise 3'-termini of the KUN replicon RNA, which is important for efficient initiation of KUN RNA replication. The fragment containing the last 1331 nucleotides of the KUN replicon sequence followed by HDVribo/SV40polyA cassette was produced by fusion PCR reaction (Karreman, 1998, *BioTechniques* 24:736–742) using Pfu DNA polymerase (Stratagene), appropriate primers and two plasmid DNAs pTMSV5A (obtained from Tom Macnaughton, Sir Albert Sakzewski Virus Research Center, Brisbane, Australia) and C20DXrep, as templates. Primers were: NS5dGDD_F (KUN NS5 sequence, forward)—5'-ctggttaact gtgtggtaaa gccctt (Referred to herein as SEQ ID NO:1)-3'; 3'UTRHDV (junction of KUN 3'end and HDV ribozyme)—5'-gagaacacag gatctgggtc ggcatggcat ct (Referred to herein as SEQ ID NO:2)-3'; SV40pA_R (SV40 polyadenylation signal, reverse)—5'-ggcctcgagc aattgttgtt gttaactt (Referred to herein as SEQ ID NO:3)-3'

Resulting PCR product was digested with XmaI (5'end) and XhoI (3'end) and cloned into XmaI/XhoI digested C20DXUb2Arep DNA, producing C20DXUb2A_HDVrep vector (FIG. 17A).

Electroporation of ~5–10 μg RNA transcribed from this construct resulted in its efficient replication in ~100% BHK21 cells compared to ~60% positive cells obtained after transfection with the same amounts of parental C20DXUb2Arep RNA (FIG. 17B).

EXAMPLE 6

DNA-Based Kunjin Replicon Expression Vector

To allow in vivo transcription of the KUN replicon RNA by cellular RNA polymerase II after transfection of the corresponding plasmid DNA we modified existing KUN replicon vector C20DXUb2A_HDVrep by inserting cytomegalovirus immediate-early (CMV-IE) enhancer/promoter region immediately upstream of the KUN replicon sequence. The fragment containing CMV-IE promoter sequence followed by 5'end of the KUN replicon sequence was produced in fusion PCR reaction (Karreman, 1998, *BioTechniques* 24:736–742) using Pfu DNA polymerase, appropriate primers and pCI (Promega) and C20DXUb2Arep plasmid DNAs as templates. Primers were: CMV_F (CMV IE promoter, forward)—5'-gcgcttaaga catgattat tgactagtta (Referred to herein as SEQ ID NO:4)-3'; CMV5'UTR (junction of CMV promoter and 5'UTR of the KUN sequence)—5'-cgtttagtga accgagtagt tcgcctgtgt ga (Referred to herein as SEQ ID NO:5)-3'; FMDV2AR (end of FMDV-2A autoprotease sequence, reverse)—5'-gtgacgcgtc ggccgggccc tgggttgga (Referred to herein as SEQ ID NO:6)-3'. Resulting PCR product was digested with EagI (3'end) and cloned into NruI (blunt)/EagI digested C20DXUb2A_HDVrep plasmid, producing pKUNRep1 vector (FIG. 18A). SV40polyA sequence was previously incorporated downstream of HDV antigenomic ribozyme sequence (see FIG. 17A) to ensure termination of transcription by RNA polymerase II.

Transfection of the plasmid DNA pKUNRep1 into BHK21 cells using FuGENE 6 transfection reagent (Boehringer Mannheim) resulted in successful detection of expression of the KUN NS3 protein (indicator of the replicating KUN replicon RNA) at 42 h post transfection (FIG. 18B).

EXAMPLE 7

Figure 19:
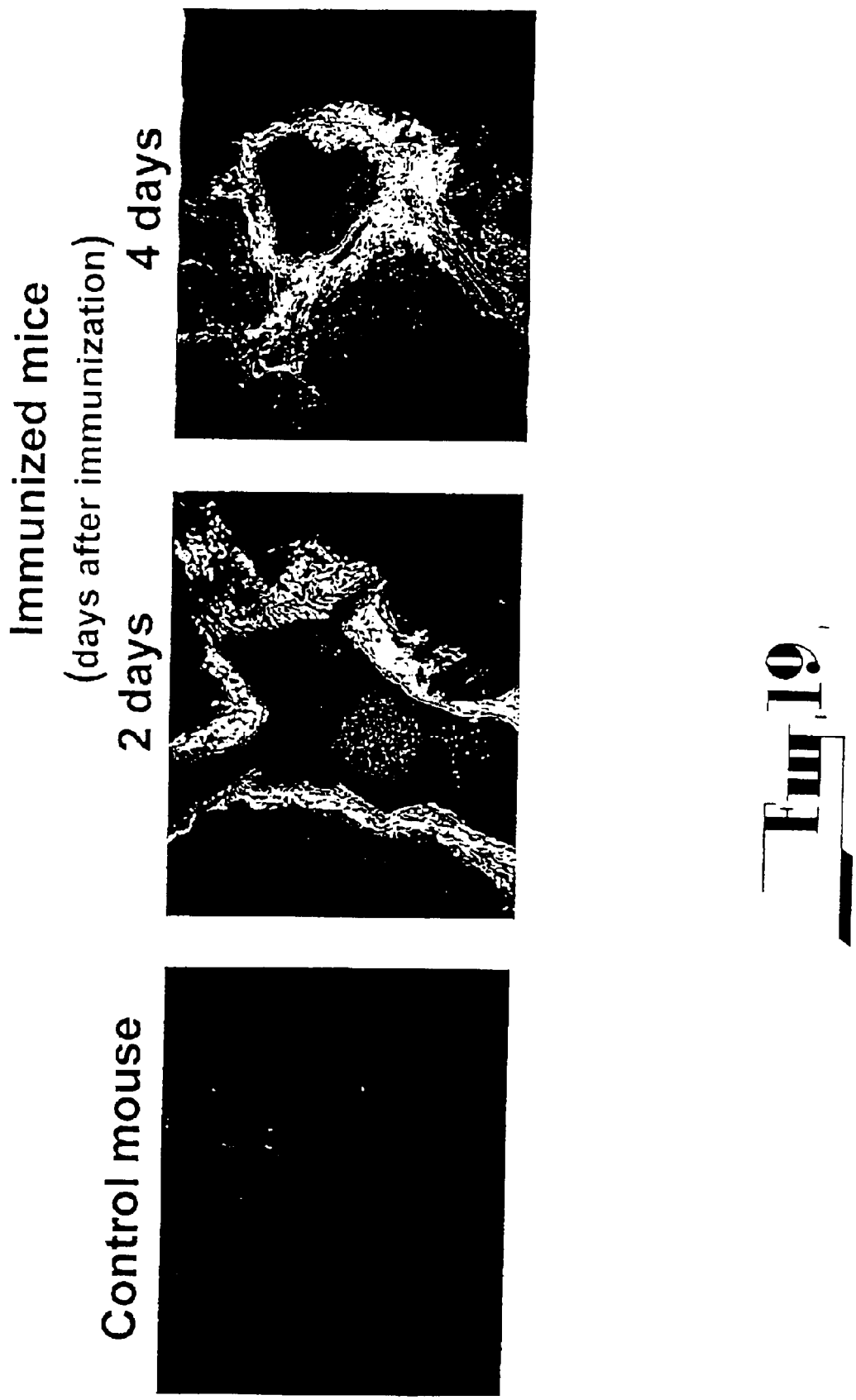
FIG. 19. illustrates Expression of GFP in mouse lung epithelium after intranasal immunization with recombinant KUN VLPs containing encapsidated C20DX/GFP/2Arep RNA.

Expression of GFP in Mouse Lung Epithelium after Intranasal Immunization with Recombinant KUN VLPs Containing Encapsidated C20DX/GFP/2Arep RNA Two female BALB/c mice were immunized intra-nasally with ~$10^6$ IU per mouse of the recombinant KUN VLPs expressing GFP (for details of the VLP preparation and determination of their titre see Example 3). Mice were anaesthetized with ketamine/xylazine (100 ul per 20 g of mouse weight) via intra-peritoneal route prior to immunization. At days 2, and 4 after immunization mice were euthanased with $CO_2$, their lungs were collected, rinsed in PBS and fixed in 4% paraformaldehyde for 2–4 hours at 4° C. Lungs were also collected from the control nonimmunized mouse using the same procedure. All the specimens were paraffin embedded and microtome sectioned at ~5 micron, mounted on a microscope slide and analyzed under ultraviolet light using FITC filter. Strong GFP fluorescence was observed in epithelial cells lining the airways passages of the lung sections prepared from mice immunized with recombinant KUN VLPs but not in the lung section prepared from the control mouse (FIG. 19). These results clearly demonstrate efficient delivery and expression of the heterologous gene in vivo using recombinant KUN VLPs.

EXAMPLE 8

Immunogenic Properties of KUN Replicon VLPs in Mice

In order to evaluate immunogenic properties of KUN replicon VLPs, three BALB/C mice were immunized intradermally (in the base of a tail) with ~$5 \times 10^5$ IU of VLPs containing packaged C20DX/GFP/2Arep RNA (see Example 3). Two weeks after immunization their serum was analyzed on the presence of anti-GFP antibodies by ELISA with purified GFP protein. The results of 50% end point titrations (ELISA $t_{50}$) for each mouse were: mouse #1—1/200, mouse #2—1/130, mouse #3—1/100. These results clearly demonstrate that specific humoral immune response to the heterologous protein encoded by the KUN replicon vector can be developed as early as at 2 weeks after only a single immunization with the recombinant KUN VLPs. It is anticipated that the antibody response will be greatly enhanced after the second immunization.

It should be understood that the foregoing description of the invention including the principles, preferred embodiments and Examples cited above are illustrative of the invention and should not be regarded as being restrictive on its scope. Variations and modifications may be made to the invention by others without departing from the spirit of that which is described as the invention and it is expressly intended that all such variations and changes which fall within this ambit are embraced thereby is intended merely to be illustrative thereof.

What is claimed is:

1. A gene expression and delivery system comprising:

(a) a replicon of Kunjin virus origin as a first vector, which is capable of receiving at least one nucleotide sequence without disrupting its replication capabilities and which is unable to express at least part or all of one or more structural proteins and/or a protein(s) or part thereof required for packaging of a Kunjin virus genome into a virus-like particle; and (b) at least a second vector that is capable of expressing Kunjin virus structural protein(s) for packaging of the replicon into a infectious Kunjin virus-like particle.

2. A gene expression and delivery system according to claim 1 wherein the replicon of Kunjin virus origin includes the nucleotide sequence for a Kunjin virus 5' untranslated region (UTR), at least a portion of the 5' coding region for Kunjin virus core protein, the nucleotide sequence coding for the Kunjin virus nonstructural proteins, and part or all of the 3'-terminal sequence of a Kunjin virus 3'UTR, required for self-replication of Kunjin virus genomic material.

3. A gene expression and delivery system according to claim 1 wherein the replicon contains a sufficient amount of Kunjin virus 5' UTR and a sufficient amount of 5' Kunjin virus coding region for core protein required for RNA replication.

4. A gene expression and delivery system according to claim 1 wherein the replicon contains a Kunjin virus 5' UTR and at least about between 60 and 80 nucleotides from the 5' coding region for flavivirus core protein.

5. A gene expression and delivery system according to claim 1 wherein the replicon contains the Kunjin virus 5' UTR and at least 60 nucleotides of the Kunjin virus 5' core protein coding region.

6. A gene expression and delivery system according to claim 1 wherein the replicon is capable of receiving at least one nucleotide sequence at any point in the replicon that does not effect processing of Kunjin virus proteins and RNA replication.

7. A gene expression and delivery system according to claim 1 wherein the replicon includes after the 3' terminal sequence of a Kunjin virus 3'UTR a sequence cassette containing a antigenomic ribozyme of the hepatitis delta virus and a SV 40 polyadenylation signal.

8. A gene expression and delivery system according to claim 1 wherein the replicon is an RNA based vector.

9. A gene expression and delivery system according to claim 1 wherein the replicon is a DNA based vector.

10. A gene expression and delivery system according to claim 1 wherein the replicon is a DNA based vector, which is capable of producing replicon RNA in cells by cellular DNA-dependent RNA polymerase from plasmid DNA incorporating mammalian expression promoters preceding the replicon sequence.

11. A gene expression and delivery system according to claim 1 wherein the replicon originates from a single Kunjin virus.

12. A gene expression and delivery system according to claim 1 wherein the second vector is heterologous in origin to the origin of the replicon.

13. A gene expression system according to claim 1 wherein the second vector is of alphavirus origin.

14. A gene expression system according to claim 1 wherein the second vector is of Semliki Forest Virus origin.

15. A gene expression system according to claim 1 wherein the second vector is of Sindbis virus origin.

16. A gene expression system according to claim 1 wherein the replicon includes part or all of the following: at least, about the first 150 nucleotides of a Kunjin virus genome; at least about the last 60 nucleotides of E protein; all of the nonstructural region; and part or all of the 3'UTR.

17. A gene expression system according to claim 1 wherein the replicon is includes part or all of the following: the first 157 nucleotides of the Kunjin virus genome, the last 66 nucleotides of E protein, the entire nonstructural region, and all of the 3'UTR.

18. A gene expression and delivery system according to claim 6 wherein the nucleotide sequence is inserted into the 3' UTR of the replicon.

19. A gene expression and delivery system according to claim 18 wherein the nucleotide sequence that is inserted into the 3' UTR of the replicon is preceded by an IRES sequence.

20. A gene expression and delivery system according to claim 8 wherein the replicon is an RNA based vector, which is capable of producing replicon RNA in in vitro transcription reactions by bacteriophage DNA-dependent RNA polymerases from a plasmid DNA that comprises one or more bacteriophage promoters preceding the replicon sequence.

21. A DNA based replicon vector of Kunjin virus origin wherein the vector comprises:
  a complementary DNA sequence that is capable of receiving at least one nucleotide sequence without disrupting its replication capabilities and which is unable to express at least part or all of a structural protein and/or a protein(s) or part thereof required for packaging of a Kunjin virus genome into a virus-like particle;
  a mammalian expression promoter 5' to the complementary DNA sequence recited in (a); and
  at least one other nucleotide sequence capable of terminating transcription of replicon RNA with a precise 3' terminus; and wherein the promoter and the one other nucleotide sequence are capable of promoting transcription and terminating same, of Kunjin virus RNA within the nucleus of a transfected cell.

22. A DNA based replicon vector according to claim 21 wherein the complementary DNA sequence includes a Kunjin virus 5' untranslated region (UTR), at least a portion of the 5' coding region for Kunjin virus core protein, the nucleotide sequence coding for the Kunjin virus nonstructural proteins, and part or all of the 3'-terminal sequence of a Kunjin virus 3'UTR, required for self-replication of Kunjin virus genomic material.

23. A DNA based replicon vector according to claim 21 wherein the mammalian expression promoter comprises a cytomegalovirus early enhancer promoter region.

24. A DNA based replicon vector according to claim 21 wherein the replicon includes at its 3'end an antigenomic ribozyme of hepatitis delta virus and simian virus 40 polyadenylation signal cassette.

25. A DNA based replicon vector according to claim 21 wherein the replicon contains a sufficient amount of the complementary DNA sequence of the Kunjin virus 5' UTR and the 5' Kunjin virus coding region for core protein required for RNA replication.

26. A DNA based replicon vector according to claim 21 wherein the replicon contains the complementary DNA sequence of a Kunjin virus 5' UTR and at least about between 60 and 80 nucleotides from the 5' coding region for Kunjin virus core protein.

27. A DNA based replicon vector according to claim 21 wherein the replicon contains the complementary DNA sequence of the Kunjin virus 5' UTR and at least 60 nucleotides of the Kunjin virus 5' core protein coding region.

28. A DNA based replicon vector according to claim 21 wherein the replicon includes the complementary DNA sequence of the nucleotide sequence for the Kunjin virus 5'UTR, at least a portion of the 5' nucleotide coding region for Kunjin virus core protein, the nucleotide coding region for Kunjin virus nonstructural proteins, a sufficient amount of the 3'-terminal region of the Kunjin virus 3'UTR required for self-replication of Kunjin virus genomic material wherein (i) the vector is is capable of receiving at least one nucleotide sequence without disrupting the replication capabilities of the vector, (ii) the nucleotide sequence is inserted into the vector in a manner which deactivates expression of at least a gene that would otherwise code for a Kunjin virus structural protein and (iii) the inserted nucleotide sequence does not encode the structural protein sequence that it deactivates.

29. A DNA based replicon vector according to claim 21 wherein the replicon is is capable of receiving at least a nucleotide sequence at any point in the replicon that does not effect processing of Kunjin virus proteins and RNA replication.

30. A DNA based replicon vector according to claim 21 wherein the nucleotide sequence is inserted into the 3' UTR of the replicon.

31. A DNA based replicon vector according to claim 21 wherein the nucleotide sequence is inserted within a structural gene.

32. A DNA based replicon vector according to claim 21 wherein the nucleotide sequence is inserted in place of one or more deleted structural genes.

33. A DNA based replicon vector according to claim 21 wherein the inserted nucleotide sequence possesses at its 3' end a 2A autoprotease sequence of foot and mouth disease virus.

34. A DNA based replicon vector according to claim 21 wherein the inserted nucleotide sequence possesses at its 5' end a mouse ubiquitin sequence.

35. A DNA based replicon vector according to claim 21 wherein the replicon originates from a single Kunjin virus.

36. A DNA based replicon vector according to claim 30 wherein the nucleotide sequence that is inserted into the 3' UTR of the replicon is preceded by an IRES sequence.

37. A DNA based replicon vector according to claim 32 wherein the nucleotide sequence that is inserted in place of the one or more deleted structural genes is followed by a termination codon and a IRES sequence.

* * * * *